United States Patent

Timmerman et al.

Patent Number: 5,756,518
Date of Patent: May 26, 1998

[54] PHENYLENE DERIVATIVES

[75] Inventors: Henk Timmerman, Voorschoten; Mingqiang Zhang, Amstelveen, both of Netherlands; Kazuhiro Onogi, Iruma, Japan; Masahiro Tamura; Tsutomu Toma, both of Higashimurayama, Japan; Yasushi Wada, Tachikawa, Japan

[73] Assignee: Kowa Co., Ltd., Nagoya, Japan

[21] Appl. No.: 824,293

[22] Filed: Mar. 26, 1997

[30] Foreign Application Priority Data

Apr. 2, 1996 [JP] Japan .................. 8-079899

[51] Int. Cl.$^6$ .................. A61K 31/47; C07D 215/12
[52] U.S. Cl. .................. 514/314; 546/174; 546/175; 546/176; 544/283; 514/258
[58] Field of Search .................. 546/174, 175, 546/176; 544/283; 514/258, 314

[56] References Cited

U.S. PATENT DOCUMENTS 5,041,453  8/1991  Huang et al. .................. 514/314

*Primary Examiner*—C. Warren Ivy
*Assistant Examiner*—Charanjit S. Aulakh
*Attorney, Agent, or Firm*—Oblon, Spivak, McClelland, Maier & Neustadt, P.C.

[57] ABSTRACT

This invention relates to a phenylene derivative represented by the following formula (1) or a salt thereof and also to a medicine containing it as an effective ingredient.

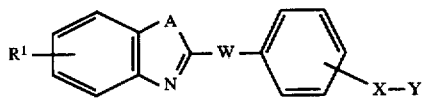

wherein $R^1$ represents H or halogen; A represents —CH=CH—, —CH=N—, —N($R^2$)—, —O— or —S—; W represents —CH=CH— or —CH$_2$O—; X represents —CH$_2$O—, —CH$_2$S—, —CH$_2$N($R^3$)—, —CH=N—, —COO— or —CONH—; Y represents

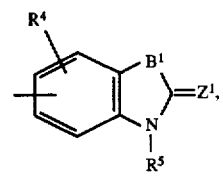

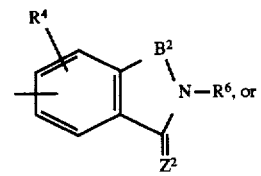

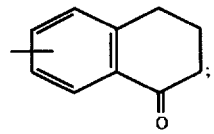

$B^1$ represents —C($R^7$)($R^8$)(CH$_2$)$_r$—, —S(O)$_m$(CH$_2$)$_n$— or —CH=C($R^9$)—; $B^2$ represents —CH$_2$CH$_2$— or —CH$_2$CH$_2$CH$_2$—; $Z^1$ and $Z^2$ each represents O or S; etc. The phenylene derivative or salt thereof has antileukotrienic action and antihistaminic action and is useful as a medicine such as an asthma preventive or curative.

10 Claims, No Drawings

PHENYLENE DERIVATIVES

BACKGROUND OF THE INVENTION a) Field of the Invention

This invention relates to phenylene derivatives or salts thereof, which are useful as medicines.

b) Description of the Related Art

Leukotrienes (LT) are associated with causes for most inflammatory diseases, especially asthma, psoriasis, rheumatism and inflammatory colitis, and are considered to play an important role in inflammatory processes through cytopathy. Leukotrienes are principal mediators of allergy and inflammation, and therefore many substances which inhibit the action and/or syntheses of leukotrienes are useful for the treatment of these diseases.

Leukotrienes are arachidonate metabolites synthesized by 5-lipoxygenase (5-LO), and consist of two groups. One of the groups is $LTB_4$ and has strong chemotaxis towards leukocytes. The other group is collectively called cysteine leukotrienes (CysLT) and includes $LTC_4$, $LTD_4$ and $LTE_4$. As biologically active substances, they have been called "slow-reacting substances of anaphylaxis (SRS-A)" for many years. CysLT binds to their receptors in human tissues to exert its action. A selective $LTD_4$ receptor inhibitor has been found to inhibit contracting actions of both $LTC_4$ and $LTD_4$ in human lung tissues, so that $LTC_4$ is suggested to bind to the same site of a receptor as $LTD_4$ (Buckner C. K. et al: Ann. NY Acad. Sci., 524, 181–6, 1988; Aharony D. et al.: New Trends in Lipid Mediators Research, Basel: Karger 67–71, 1989). $LTE_4$ is also considered to act via the same receptor as $LTD_4$, but is called a partially active substance for its lower potency.

On the other hand, histamine exhibits bronchial smooth muscle constricting action and capillaropenetration accelerating action as a result of its binding to the $H_1$ receptor in cell membranes, and is an important mediator in allergic diseases. Histamine is believed to cause aggravation of asthmatic symptoms by its bronchoconstricting action and also to increase transudation of blood components into intercellular spacings due to accelerated capillaropenetration and hence to take part in the formation of edema seen in allergic rhinitis and conjunctivitis. For the treatment of these allergic diseases, antihistaminic agents are therefore used. These antihistaminic agents are however not considered to be significantly effective for severe allergic diseases such as asthma. Especially in a late asthmatic response of asthma, the symptom of airway constriction which is typical to asthma is observed due to infiltration of inflammatory cells on the bronchial mucosa, oversecretion of mucus and the like. Pharmaceuticals of a new type are therefore desired for its treatment.

Described specifically, a severe allergic disease such as asthma is considered to develop, as successive morbid conditions, an immediate asthmatic response such as bronchial constriction and edematous formation, in which a mediator such as histamine takes principal part, and a late asthmatic response such as airway constriction due to cell infiltration and mucus secretion in which a leukotriene or the like takes part.

For the prevention or curation of a variety of allergic diseases, especially asthma, a compound having antagonism against both an $LTD_4$ receptor and a histamine $H_1$ receptor is considered to become an effective pharmaceutical.

In addition to such marked peripheral action, leukotrienes have also been reported to have certain relevance to causes for cerebropathy such as cerebral ischemia and cerebral apoplexy (Masamune H. and Melvin L. S.: Ann. Rep. Med. Chem., 24, 71–79, 1989). It has also been reported that upon occurrence of prochepharic ischemia, the concentration of $LTC_4$ produced in neurocytes arises in the hippocampus (13.37±0.24 pmol/g-tissue) and the cerebral cortex (3.29±1.09 pmol/g) (Ohtsuki T. et al.: Am. J. Physiol., 37, H1249–57, 1995). Further, it has also been reported that intravenous administration of FPL55712, an $LTD_4$ antagonist, after occurrence of ischemia significantly inhibited increase and aggravation of cortical edema (Watanabe T. et al.: J. Pharmacol. Exp. Ther., 271, 1624–29, 1994).

Accordingly, leukotriene receptor antagonistic compounds are considered to become effective pharmaceuticals for such cerebropathy.

It is however the current circumstances that no compound has been found with fully satisfactory antagonism against both an $LTD_4$ receptor and a histamine $H_1$ receptor. Further, all the $LTD_4$ antagonists which have been developed so far contain at least one acidic group, so that these $LTD_4$ antagonists are hydrophilic compounds having high polarity. They are thus unavoidably insufficient in absorption and brain penetration upon inhalative administration or oral administration. This is believed to have led to the increased doses of these pharmaceuticals and hence, to the development of side effects.

SUMMARY OF THE INVENTION

Therefore, an object of the present invention is to provide a medicine comprising as an effective ingredient a compound having both antileukotrienic action and antihistaminic action, and another object of the present invention is to provide a medicine comprising as an effective ingredient a strong leukotriene receptor antagonistic compound.

With the foregoing current circumstances in view, the present inventors have conducted an extensive investigation with a view to obtaining a strong leukotriene receptor antagonistic compound which has both antileukotrienic action and antihistaminic action. As a result, it has been found that a compound represented by the following formula (1) is useful, leading to the completion of the present invention.

In one aspect of the present invention, there is accordingly provided a phenylene derivative represented by the following formula (1) or a salt thereof:

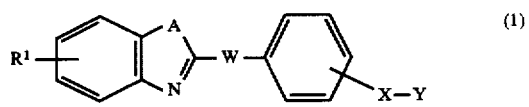

wherein $R^1$ represents a hydrogen atom or a halogen atom,

A represents —CH=CH—, —CH=N—,

—O— or —S—, $R^2$ being a lower alkyl group or an alkoxyalkyl group,

W represents —CH=CH— or —CH$_2$O—,

X represents —CH$_2$O—, —CH$_2$S—,

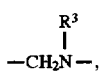

—CH=N—, —COO— or —CONH—, R$^3$ being a hydrogen atom or a lower alkyl group,

Y represents the following formula (a), (b) or (c):

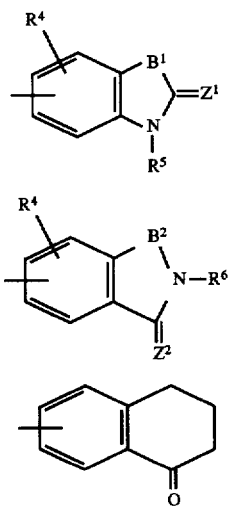

wherein
R$^4$ is a hydrogen atom or a lower alkyl group,
B$^1$ represents

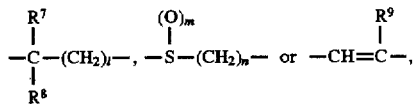

and R$^8$ each being a hydrogen atom or a lower alkyl group, R$^9$ being a hydrogen atom, a cyano group, a halogen atom, a carboxyl group or a tetrazolyl group, l and m being a value of from 0 to 2, and n being a value of 1 to 2, R$^5$ represents a hydrogen atom or a lower alkyl group,
Z$^1$ represents an oxygen atom or a sulfur atom,
B$^2$ represents —CH$_2$CH$_2$— or —CH$_2$CH$_2$CH$_2$—,
R$^6$ represents a hydrogen atom or a lower alkyl group,
Z$^2$ represents an oxygen atom or a sulfur atom, or Z$^2$ and R$^6$ are coupled together with the adjacent nitrogen atom to form a tetrazolyl group.

In another aspect of the present invention, there is also provided a medicine comprising as an effective ingredient a phenylene derivative represented by the formula (1) or a salt thereof.

In a further aspect of the present invention, there is also provided a medicinal composition comprising a phenylene derivative represented by the formula (1) or a salt thereof and a pharmaceutically acceptable carrier.

In a still further aspect of the present invention, there is also provided a method for treating an allergic disease such as asthma, allergic rhinitis, allergic conjunctivitis, atopic dermatitis, urticaria or psoriasis, rheumatism, inflammatory colitis, cerebral ischemia or cerebral apoplexy, which comprises administering an effective amount of a phenylene derivative represented by the formula (1) or a salt thereof to a patient.

The phenylene derivative (1) or the salt thereof according to the present invention has antileukotrienic action and antihistaminic action and is useful as a medicine such as asthma preventive or curative.

DETAILED DESCRIPTION OF THE INVENTION AND PREFERRED EMBODIMENTS

In compound (1), examples of the halogen atoms represented by R$^1$ and R$^9$ include fluorine, chlorine, bromine and iodine atoms, among which a chlorine atom is preferred.

Illustrative of the lower alkyl groups represented by R$^2$, R$^3$, R$^4$, R$^5$, R$^6$, R$^7$ and R$^8$ are alkyl groups having 1–6 carbon atoms. These alkyl groups include both linear and branched alkyl groups. More preferred alkyl groups include methyl, ethyl, n-propyl, isopropyl, n-butyl, isobutyl, t-butyl, pentyl and n-hexyl, with methyl and n-hexyl being particularly preferred.

Illustrative of the alkoxyalkyl group represented by R$^2$ are C$_{1-6}$ alkoxy C$_{1-6}$ alkyl groups, specifically methoxymethyl, methoxyethyl, methoxypropyl, methoxybutyl, ethoxymethyl, ethoxyethyl, ethoxypropyl, ethoxybutyl, propoxymethyl, propoxyethyl, propoxypropyl and propoxybutyl, with ethoxyethyl being particularly preferred.

Examples of the group represented by the formula (a) include groups represented by the following formula (a-1) to formula (a-7).

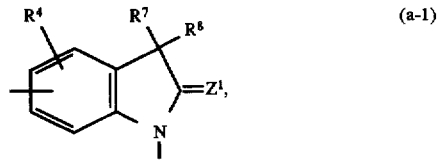
(a-1)

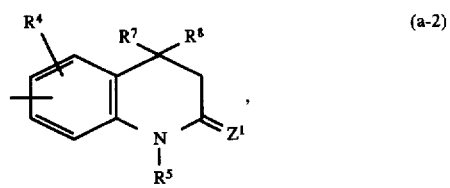
(a-2)

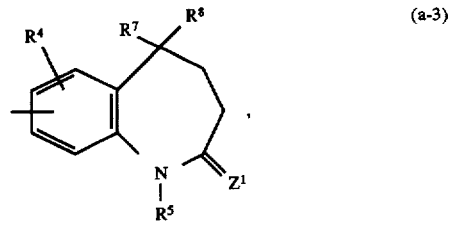
(a-3)

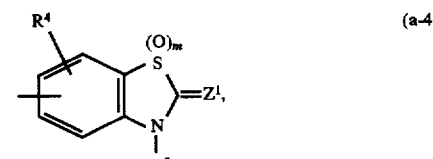
(a-4)

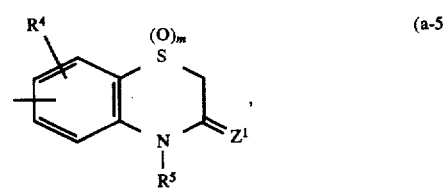
(a-5)

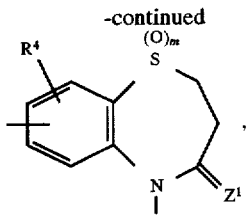

(a-6)

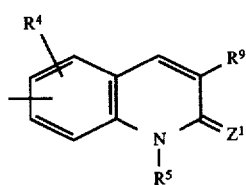

(a-7)

wherein $R^4$, $R^5$, $R^7$, $R^8$, $R^9$, $Z^1$ and m have the same meanings as defined above.

Further, examples of the group represented by the formula (b) include groups represented by the following formula (b-1) and formula (b-2).

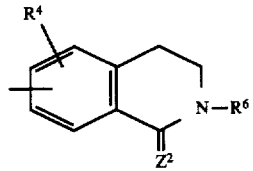

(b-1)

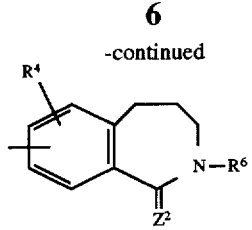

(b-2)

wherein $Z^2$, $R^4$ and $R^6$ have the same meanings as defined above.

No particular limitation is imposed on the salt of the compound (1) of the present invention, insofar as it is a pharmacologically acceptable salt. Illustrative are mineral acid addition salts such as the hydrochloride, hydrobromide, hydroiodide, sulfate and phosphate; organic acid addition salts such as the benzoate, methanesulfonate, ethanesulfonate, benzenesulfonate, p-toluenesulfonate, oxalate, maleate, fumarate, tartrate and citrate; and metal salts such as the sodium salt, potassium salt, calcium salt, magnesium salt, manganese salt, iron salt and aluminum salt.

Further, the compound (1) of the present invention may also exist in the form of solvates represented by the hydrate. Such solvates are also included in the present invention.

The compound (1) of the present invention can be prepared, for example, in accordance with the following reaction scheme.

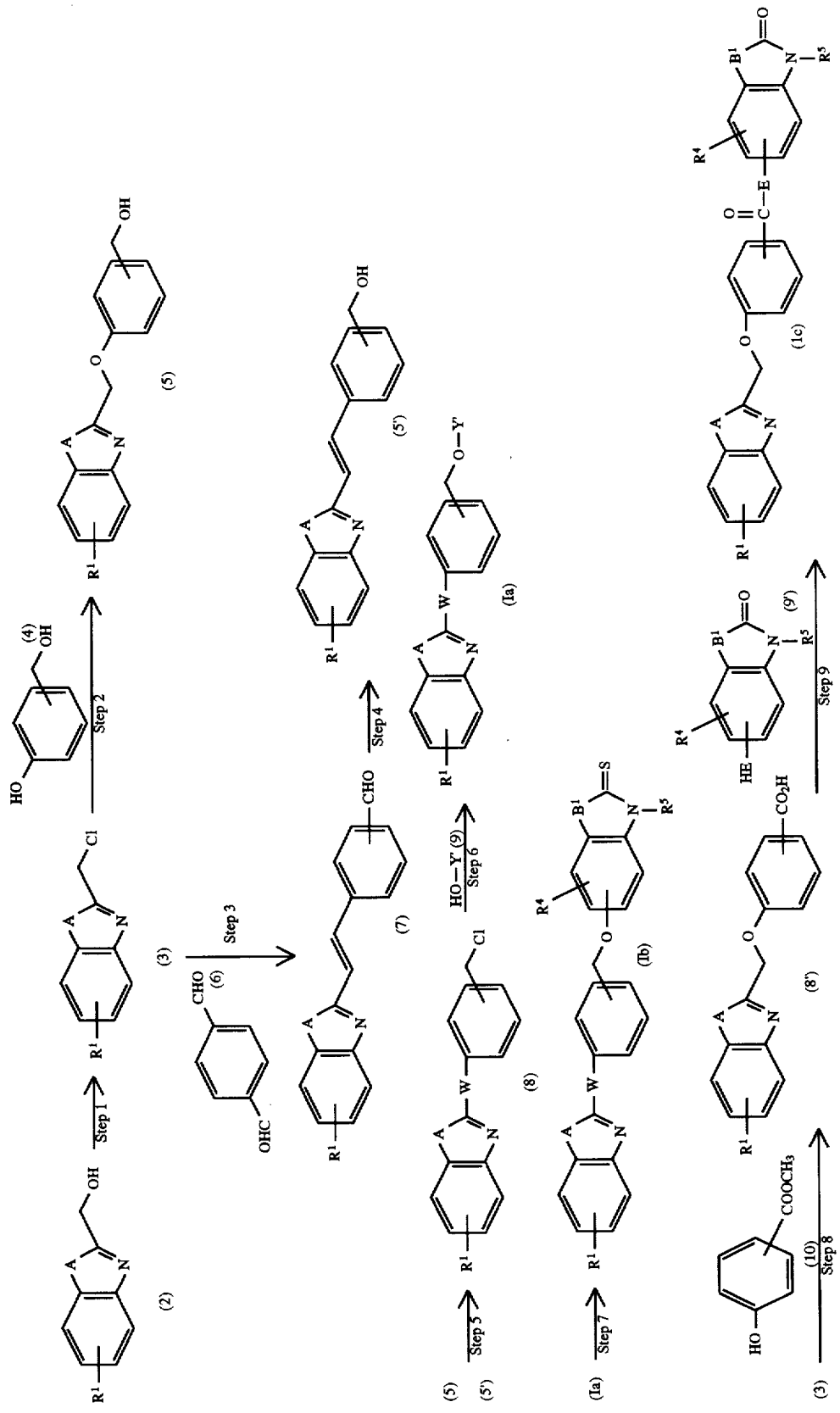

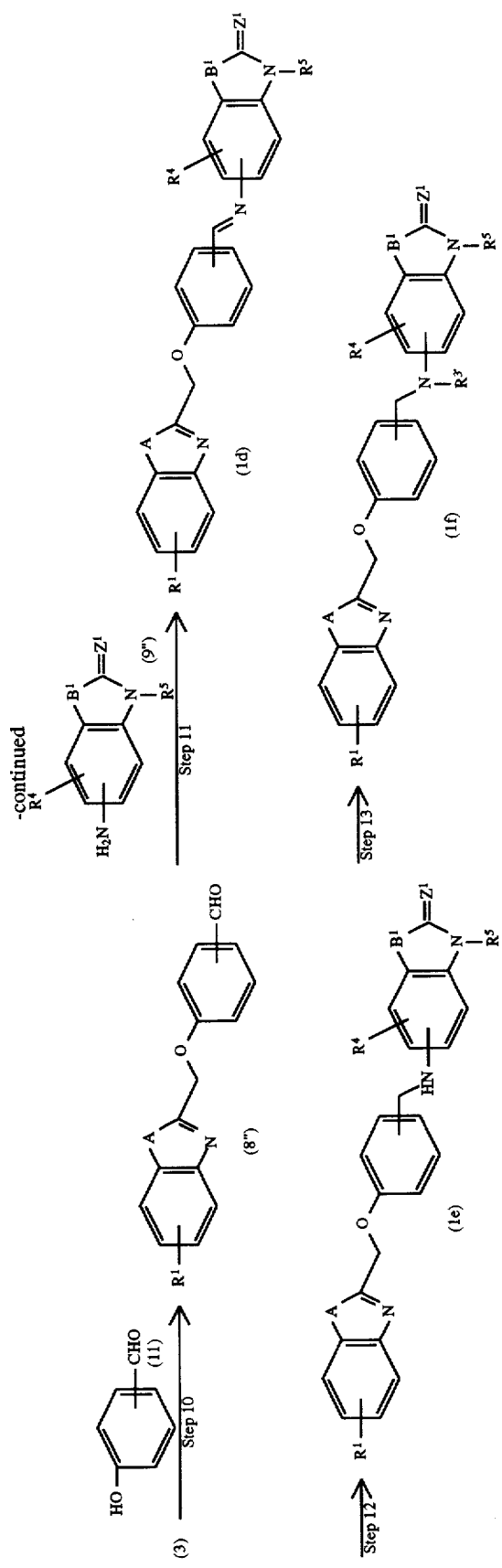

wherein Y' represents

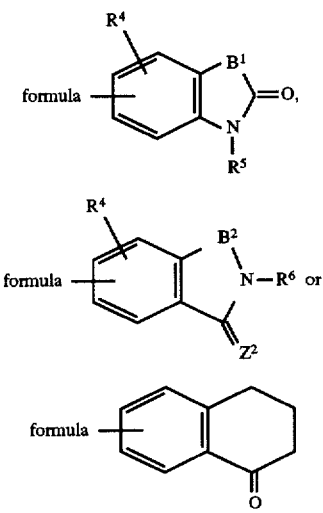

R$^{3'}$ represents a lower alkyl group, E represents an oxygen atom or NH, and R$^1$, R$^4$, R$^5$, R$^6$, Z$^1$, Z$^2$, A, B$^1$, B$^2$ and W have the same meanings as defined above.

Namely, subsequent to the conversion of the compound (2) into the chlorinated derivative (3), the chlorinated derivative (3) is reacted with the phenol compound (4) to obtain the compound (5). On the other hand, the chlorinated derivative (3) and the aldehyde compound (6) are subjected to a Witting reaction so that the compound (5') is obtained. This compound (5) or compound (5') is converted into the chlorinated derivative (8), followed by the reaction with the compound (9) to obtain the invention compound (1a). By sulfurizing the compound (1a), the invention compound (1b) is obtained. Further, the compound (8') is obtained from the compound (3), which is then reacted with the compound (9') to obtain the invention compound (1c). In addition, the compound (3) and the hydroxybenzaldehyde compound (11) are reacted to obtain the invention compound (1d). Reduction of the compound (1d) then provides the invention compound (1e), whose alkylation in turn provides the invention compound (1f).

Incidentally, as the compound (2), compound (9) and compound (9'), either conventionally known compounds or those prepared by conventionally known processes can be used.

A description will next be made about the individual steps of the above reaction scheme.

Step 1

The compound (3) is obtained by reacting the compound (2) with an excess amount of SOCl$_2$ in an inert solvent such as THF (tetrahydrofuran), CHCl$_3$ or CH$_2$Cl$_2$ at a temperature of from 0° C. to reflux temperature (preferably at room temperature) for 1 to 24 hours.

Step 2

The compound (5) is obtained by reacting equimolar amounts of the compound (3) and the compound (4) in the presence of an excess amount of a base such as K$_2$CO$_3$ or Na$_2$CO$_3$ in a polar solvent such as DMF (N,N-dimethylformamide), DMSO (dimethylsulfoxide) or HMPA (hexamethylphosphoramide) at a temperature of from 0° C. to reflux temperature (preferably at room temperature to 60° C.) for 1 to 7 days.

Step 3

The compound (3) is refluxed together with an equimolar amount of PPh$_3$ ("Ph" stands for a phenyl group) in an inert solvent such as benzene, toluene or xylene for 12 to 48 hours to synthesize the corresponding phosphonium salt. The phosphonium salt is reacted with an equimolar amount of t-BuOK (potassium tertbutoxide) in dry THF under a nitrogen or argon gas stream to prepare a Wittig reagent, to which an equimolar amount of the compound (6) is added, followed by refluxing for 1 to 12 hours to obtain the compound (7).

Step 4

The compound (5') is obtained by reacting the compound (7) with NaBH$_4$ in a polar solvent such as methanol or ethanol at a temperature of from 0° C. to reflux temperature (preferably at room temperature) for 1 to 24 hours.

Step 5

The compound (8) is obtained by reacting the compound (5) or the compound (5') with an excess amount of SOCl$_2$ in an inert solvent such as THF, CHCl$_3$ or CH$_2$Cl$_2$ at a temperature of from 0° C. to reflux temperature (preferably at room temperature) for 1 to 24 hours.

Step 6

The invention compound (1a) is obtained by reacting equimolar amounts of the compound (8) and the compound (9) in the presence of an excess amount of a base such as K$_2$CO$_3$ or Na$_2$CO$_3$ in a polar solvent such as DMF, DMSO or HMPA at a temperature of from 0° C. to reflux temperature (preferably at room temperature to 60° C.) for 1 to 7 days.

Step 7

The compound (1b) is obtained by reacting the compound (1a) with a sulfurizing agent such as P$_2$S$_5$ or the Lawesson's reagent in an inert solvent such as benzene, toluene or xylene at reflux temperature for 1 to 6 hours.

Step 8

The methyl ester derivative of the compound (8') is obtained by reacting equimolar amounts of the compound (3) and the compound (10) in the presence of an excess amount of a base such as K$_2$CO$_3$ or Na$_2$CO$_3$ in a polar solvent such as DMF, DMSO or HMPA at a temperature of from 0° C. to reflux temperature (preferably at room temperature to 60° C.) for 1 to 7 days. The methyl ester derivative is reacted with 2 to 4 equivalents of NaOH in water-containing MeOH for 1 to 12 hours, whereby the compound (8') is obtained.

Step 9

The invention compound (1c) is obtained by reacting equimolar amounts of the compound (8') and the compound (9') in the presence of a coupling agent such as DCC (N,N'-dicyclohexylcarbodiimide) or WSC.HCl in a polar solvent such as DMF, DMSO or HMPA at a temperature of from 0° C. to reflux temperature (preferably at room temperature to 60° C.) for 1 to 14 days.

Step 10

The aldehyde compound (8") is obtained by reacting equimolar amounts of the compound (3) and the compound (11) in the presence of a base such as K$_2$CO$_3$, Na$_2$CO$_3$ or triethylamine and a phase transfer catalyst such as tetrabutylammonium bromide or tetraethylammonium bromide in a polar solvent such as DMF, DMSO or HMPA at a temperature of from 0° C. to reflux temperature (preferably at room temperature to 60° C.) for 1 to 14 days.

Step 11

The invention compound (1d) is obtained by reacting equimolar amounts of the compound (8") and the compound (9") in a polar solvent such as ethanol, methanol, butanol, DMF, DMSO or HMPA at a temperature of from 0° C. to reflux temperature (preferably at room temperature to 100° C.) for 1 to 14 days.

Step 12

The invention compound (1e) is obtained by reacting the compound (1d) further in one of polar solvents such as methanol, ethanol, DMF, DMSO, HMPA or a mixed solvent thereof (preferably in a mixed solvent of DMF and methanol) in the presence of a reducing agent, for example, NaBH$_4$ at 0° C. to 60° C. (preferably at 0° C. to room temperature) for 30 minutes to 24 hours.

Step 13

The invention compound (1f) is obtained by reacting the compound (1e) further with an alkyl halide in the presence of a base such as K$_2$CO$_3$, Na$_2$CO$_3$ or triethylamine and a phase transfer catalyst such as tetrabutylammonium bromide or tetraethylammonium bromide in a polar solvent such as DMF, DMSO or HMPA at a temperature of from 0° C. to reflux temperature (preferably at room temperature to 60° C.) for 1 to 14 days.

Further, to obtain the invention compound (1a) or (1c) in which B is —(O)$_m$.CH$_2$— or —S(O)$_m$.CH$_2$CH$_2$— (m': 1 or 2) in the formula (1) from the compound (1a) or (1c) in which B is —SCH$_2$— or —SCH$_2$CH$_2$— in the formula (1), it is only necessary to react the compound (1a) or (1c) with m-CPBA or H$_2$O$_2$ in a molar amount 1 or 2 times as much as the compound (1a) or (1c) in a solvent such as CHCl$_3$, CH$_2$Cl$_2$ or AcOH (Ac: acetyl group) at 0° C. to room temperature for 1 to 72 hours.

The above-described target compounds can each be obtained by treating the reaction mixture by a method known per se in the art and if necessary, can be purified using a conventional purification method such as column chromatography. By a method known per se in the art, they can be converted into the above-described desired salts as needed.

As will be demonstrated subsequently in Examples, the invention compound (1) or salt thereof available as described above has excellent antileutrienic action and antihistaminic action, and is useful as a medicine such as a preventive or curative for asthma, allergic rhinitis, allergic conjunctivitis, atopic dermatitis, urticaria, psoriasis, rheumatism, inflammatory colitis, cerebral ischemia or cerebral apoplexy.

The medicine according to the present invention comprises the above-described compound (1) or a salt or hydrate thereof as an effective ingredient. Its administration forms include, for example, oral administration forms such as tablets, capsules, granules, powders and syrups; and parenteral administration forms such as intravenous injections, intramuscular injections, suppositories, inhalative agents, percutaneous absorption agents, eye drops and nasal drops. Upon production of medicinal preparations in such various administration forms, the effective ingredient can be used either singly or by suitably combining the same with one or more pharmacologically acceptable vehicles such as excipients, binders, extenders, disintegrants, surfactants, lubricants, dispersants, buffers, preservatives, corrigents, perfumes, coating materials, carriers, diluents and the like.

The dosage of the medicine according to the present invention varies depending on the age, body weight, conditions, administration form, administration frequency and the like. In general, however, it is preferred to orally or parenterally administer to an adult the effective ingredient in an amount of about 1 to 1,000 mg per day at once or in several portions.

The present invention will next be described in further detail by the following Examples. It should however be borne in mind that the present invention is by no means limited to these Examples.

PREPARATION EXAMPLE 1

Synthesis of 3-(2-quinolinylmethoxy)benzyl chloride

SOCl$_2$ (2 ml) was added to a solution of 3.58 g (13.5 mmol) of 3-(2-quinolinylmethoxy)benzyl alcohol in 100 ml of CHCl$_3$, followed by stirring at room temperature for 24 hours. A small amount of MeOH was added to the reaction mixture and the solvents were distilled off under reduced pressure, whereby the title compound was obtained as white powder.

EXAMPLE 1

Synthesis of 3-cyano-6-[3-(2-quinolinylmethoxy)-benzyloxy]-1,2-dihydroquinolin-2-one 3-(2-quinolinylmethoxy)benzyl chloride (3.49 g, 12.3 mmol) was added to a solution of 2.45 g (12.3 mmol) of 3-cyano-6-hydroxy-1,2-dihydroquinolin-2-one in 100 ml of DMF, followed by the further addition of 2.04 g (14.8 mmol) of K$_2$CO$_3$ and 396 mg (1.23 mmol) of tetra-n-butylammonium bromide. The resulting mixture was stirred under an argon gas stream at room temperature for 24 hours. The reaction mixture was concentrated under reduced pressure, followed by the addition of CHCl$_3$—MeOH and water to extract the reaction product into the organic layer. The organic layer was dried over Na$_2$SO$_4$ and then concentrated under reduced pressure. The residue was subjected to chromatography on a silica gel column. Subsequent to elution with CHCl$_3$, recrystallization was conducted from a CHCl$_3$—MeOH mixed solvent, whereby 250 mg of the title compound were obtained as yellow powder (yield: 4.7%). Melting point: 145°–147° C. (decomposed).

$^1$H-NMR(CDCl$_3$—MeOH)$\delta$(ppm): 5.31(2H,s,—C$_6$H$_4$—CH$_2$—), 5.51(2H,s,C$_9$H$_6$N—CH$_2$—), 6.74(1H,br,Ar-H), 6.83–7.00(3H,m,Ar-H), 7.09–7.31(3H,m,Ar-H), 7.56–7.64 (2H,m,Ar-H), 7.79(1H,ddt,J=8.5,7.1,1.5 Hz,Ar-H), 7.88 (1H,d,J=8.1 Hz,Ar-H), 8.03(1H,d,J=8.8 Hz,Ar-H), 8.18(1H, s,Ar-H), 8.20(1d,d,J=8.8 Hz,Ar-H).

IR(KBr)cm$^{-1}$: 3059, 2225, 1648, 1613, 1569, 1451, 1252, 1070, 774.

EXAMPLES 2–17

The following compounds were obtained in a similar manner as in Example 1.

TABLE 1

| Ex. | Compound (1) | mp(°C.) |
|---|---|---|
| 2 | 8-Methyl-5-[3-(2-quinolinylmethoxy)-benzyloxy]-1,2-dihydroquinolin-2-one | 205–207 |
| 3 | 3-Cyano-8-methyl-5-[3-(2-quinolinyl-methoxy)benzyloxy]-1,2-dihydro-quinolin-2-one | 224–225 |
| 4 | 2-Chloro-8-methyl-5-[3-(2-quinolinyl-methoxy)benzyloxy]-1,2-dihydro-quinolin-2-one | 217–219 |
| 5 | 8-Methyl-5-[3-(2-quinolinylmethoxy)-benzyloxy]-1,2,3,4-tetrahydro-quinolin-2-one | 172–174 |
| 6 | 6-[3-(2-Quinolinylmethoxy)benzyloxy-1,2,3,4-tetrahydroquinolin-2-one | 158–159 (dec) |
| 7 | 7-[3-(2-Quinolinylmethoxy)benzyloxy-1,2,3,4-tetrahydroquinolin-2-one | 180–183 (dec) |
| 8 | 8-[3-(2-Quinolinylmethoxy)benzyloxy]-1,2,3,4-tetrahydroquinolin-2-one | 124–125 |
| 9 | 7-[3-(2-Quinolinylmethoxy)benzyloxy]-2,3,4,5-tetrahydrobenz[b]azepin-2-one | 150–151 |
| 10 | 7-[3-(2-Quinolinylmethoxy)benzyloxy]-3,4-dihydro-2H-1,4-benzothiazin-3-one | 160–162 |

TABLE 1-continued

| Ex. | Compound (1) | mp(°C.) |
|---|---|---|
| 11 | 8-[3-(2-Quinolinylmethoxy)benzyloxy]-2,3,4,5-tetrahydro-1,5-benzo-thiazepin-4-one | 139–140 |
| 12 | 4-[3-(2-Quinolinylmethoxy)benzyloxy]-2,3-dihydro-1H-indol-2-one | 193–195 |
| 13 | 4-[3-(2-Quinolinylmethoxy)benzyloxy]-3,3,7-trimethyl-2,3-dihydro-1H-indol-2-one | 178–180 |
| 14 | 3,3'-Dimethyl-5-[3-(2-quinolinyl-methoxy)benzyloxy]-2,3-dihydro-1H-indol-2-one | 162–163 |
| 15 | 3,3-Dimethyl-6-[3-(2-quinolinyl-methoxy)benzyloxy]-2,3-dihydro-1H-indol-2-one | 161–162 |
| 16 | 3,3-Dimethyl-4-(n-hexyl)-6-[3-(2-quinolinylmethoxy)benzyloxy]-2,3-dihydro-1H-indol-2-one | 117–119 |
| 17 | 3,3-Dimethyl-7-[3-(2-quinolinyl-methoxy)benzyloxy]-2,3-dihydro-1H-indol-2-one | 136–139 (dec) |

PREPARATION EXAMPLE 2

Synthesis of 4-(2-quinolinylmethoxy)benzyl Chloride

In a similar manner as in Preparation Example 1, the title compound was obtained as white powder from 4-(2-quinolinylmethoxy)benzyl alcohol.

EXAMPLE 18

Synthesis of 3,3-dimethyl-5-[4-(2-quinolinylmethoxy)benzyloxy]-2,3-dihydro-1H-indol-2-one 4-(2-Quinolinylmethoxy)benzyl chloride (567 mg, 2 mmol) was dissolved in 20 ml of DMF, followed by the addition of 354 mg (2 mmol) of 3,3-dimethyl-5-hydroxy-2,3-dihydro-1H-indol-2-one, 64 mg (0.2 mmol) of tetra-n-butylammonium bromide and 691 mg (5 mmol) of $K_2CO_3$. The resultant mixture was stirred under an argon gas stream at 50° C. for 72 hours. After the solvent was distilled off, water was added, and the thus-formed mixture was extracted twice in a $CHCl_3$—MeOH (3:1) mixed solvent. The extract was dried over $MgSO_4$ and then concentrated under reduced pressure. The residue was subjected to chromatography on a silica gel column. Subsequent to elution with $CHCl_3$, recrystallization was conducted from AcOEt-hexane, whereby 199 mg of the title compound were obtained as pale yellow powder (yield: 23.5%).

Melting point: 172°–175° C. (decomposed).

$^1$H-NMR($CDCl_3$)δ(ppm): 1.37(6H,s,C3-Me×2), 4.94(2H,s,—$C_6H_4$—$CH_2$—), 5.40(2H,s,$C_9H_6N$—$CH_2$—), 6.78–6.80 (2H,m,Ar-H), 6.85(1H,d,J=2.2 Hz,Ar-H), 7.02(2H,d,J=8.8 Hz,—$C_6H_4$—$CH_2$—), 7.36(2H,d,J=8.8 Hz,—$C_6H_4$—$CH_2$—), 7.55(1H,dt,J=8.1,1.5 Hz,Ar-H), 7.67(1H,d,J=8.6 Hz,Ar-H), 7.74(1H,dt,J=8.5,1.5 Hz,Ar-H), 7.83(1H,d,J=8.1 Hz,Ar-H), 8.09(1H,d,J=8.5 Hz,Ar-H), 8.20(1H,d,J=8.5 Hz,Ar-H), 8.29(1H,brs,CONH).

IR(KBr)cm$^{-1}$: 1727, 1613, 1601, 1515, 1493, 1456, 1429, 1382, 1301, 1277, 1251, 1224, 1196, 1174, 1115, 1072, 1062, 1027, 1013, 952, 934, 903, 872, 832, 804, 785, 754, 651, 619, 535, 525, 477, 460.

EXAMPLES 19–30

In a similar manner as in Example 18, the following compounds were obtained.

TABLE 2

| Ex. | Compound (1) | mp(°C.) |
|---|---|---|
| 19 | 3-Cyano-8-methyl-5-[4-(2-quinolinyl-methoxy)benzyloxy]-1,2-dihydro-quinolin-2-one | 267–270 (dec) |
| 20 | 3-Chloro-8-methyl-5-[4-(2-quinolinyl-methoxy)benzyloxy]1,2-dihydro-quinolin-2-one | 253–256 (dec) |
| 21 | 8-Methyl-5-[4-(2-quinolinylmethoxy)-benzyloxy]-1,2,3,4-tetrahydro-quinolin-2-one | 193–195 (dec) |
| 22 | 6-[4-(2-Quinolinylmethoxy)benzyloxy-1,2,3,4-tetrahydroquinolin-2-one | 186–189 |
| 23 | 7-[4-(2-Quinolinylmethoxy)benzyloxy-1,2,3,4-tetrahydroquinolin-2-one | 199–202 |
| 24 | 8-[4-(2-Quinolinylmethoxy)benzyloxy]-1,2,3,4-tetrahydroquinolin-2-one | 133–134 |
| 25 | 7-[4-(2-Quinolinylmethoxy)benzyloxy]-2,3,4,5-tetrahydro-1H-benzo[b]azepin-2-one | 181–183 |
| 26 | 7-[4-(2-Quinolinylmethoxy)benzyloxy]-3,4-dihydro-2H-1,4-benzothiazin-3-one | 229–232 (dec) |
| 27 | 4-[4-(2-Quinolinylmethoxy)benzyloxy]-3,3,7-trimethyl-2,3-dihydydro-1H-indol-2-one | 209–211 |
| 28 | 3,3-Dimethyl-6-[4-(2-quinolinyl-methoxy)benzyloxy]-2,3-dihydro-1H-indol-2-one | 191–196 (dec) |
| 29 | 3,3-Dimethyl-4-(n-hexyl)-6-[4-(2-quinolinylmethoxy)benzyloxy]-2,3-dihydro-1H-indol-2-one | 134–136 |
| 30 | 3,3-Dimethyl-7-[4-(2-quinolinyl-methoxy)benzyloxy]-2,3-dihydro-1H-indol-2-one | 150–153 (dec) |

PREPARATION EXAMPLE 3

Synthesis of 3-(7-chloro-2-quinolinylmethoxy)benzyl chloride

In a similar manner as in Preparation Example 1, the title compound was obtained from 3-(7-chloro-2-quinolinylmethoxy)benzyl alcohol.

EXAMPLE 31

Synthesis of 7-[3-(7-chloro-2-quinolinylmethoxy)benzyloxy]-1,2,3,4-tetrahydroquinolin-2-one A mixture of 0.326 g (2 mmol) of 7-hydroxy-1,2,3,4-tetrahydroquinolin-3-one, 0.609 g (5 mmol) of $K_2CO_3$, 0.075 g (0.25 mmol) of tetra-n-butylammonium bromide, 40 ml of DMF and 0.636 g (2 mmol) of 3-(7-chloro-2-quinolinylmethoxy)benzyl chloride was stirred at room temperature for 3 days. Insoluble matter was removed and the solvent was then distilled off. The residue was subjected to chromatography on a silica gel column. Subsequent to elution with $CHCl_3$, recrystallization was conducted from acetone, whereby 0.245 g of the title compound was obtained as pale yellow powder (yield: 27.6%).

Melting point: 150°–151° C.

$^1$H-NMR($CDCl_3$)δ(ppm): 2.53–2.67(2H,m,$CH_2$ at C3), 2.81–2.94(2H,m,$CH_2$ at C4), 5.00(2H,s,—$C_6H_4$—$CH_2$), 5.37(2H,s,$C_9H_5NCl$—$CH_2$—), 6.36(1H,d,J=2.4 Hz,C8-H), 6.55(1H,dd,J=8.8,2.4 Hz,C6-H), 6.91–7.14(4H,m,Ar-H), 7.32(1H,d,J=7.8 Hz,Ar-H), 7.50(1H,dd,J=8.8,1.9 Hz,Ar-H), 7.67(1H,d,J=8.8 Hz,Ar-H), 7.76(1H,dd,J=8.8,1.9 Hz,Ar-H), 8.04(1H,brs,CONH), 8.07(1H,d,J=1.9 Hz,Ar-H), 8.16(1H,d, J=8.3 Hz,Ar-H).

IR(KBr)cm$^{-1}$: 1681, 1628, 1614, 1595, 1521, 1492, 1375, 1274, 1198, 1184, 852.

EXAMPLE 32

Synthesis of 7-[3-(7-chloro-2-quinolinylmethoxy)benzyloxy]-3,4-dihydro-2H-1,4-benzothiazin-3-one In a similar manner as in Example 31, the title compound was obtained as yellow powder from 7-hydroxy-3,4-dihydro-2H-1,4-benzothiazin-3-one (yield: 42.9%).
Melting point: 163°–165° C. (CHCl$_3$)
$^1$H-NMR(DMSO-d$_6$)δ(ppm): 3.42(2H,s,CH$_2$— at C2), 5.03 (2H,s,—C$_6$H$_4$—CH$_2$O), 5.38(2H,s,CH$_2$O—C$_6$H$_4$—), 6.73–7.05(5H,m,Ar-H), 7.13(1H,s,Ar-H), 7.31(1H,t,J=7.8 Hz,Ar-H), 7.60–7.74(2H,m,Ar-H), 7.98–8.12(2H,m,Ar-H), 8.46(1H,d,J=8.8 Hz,Ar-H), 10.40(1H,s,CONH).
IR(KBr)cm$^{-1}$: 3190, 3083, 3045, 2963, 2909, 1671(CONH), 1613, 1587, 1498, 1290, 1270, 1238, 1156, 1068, 842, 766.

PREPARATION EXAMPLE 4

Synthesis of 3-(2-quinazolinylmethoxy)benzyl alcohol

To a solution of 5.00 g (28 mmol) of 2-chloromethylquinazoline in 50 ml of DMF, 4.26 g (31 mmol) of K$_2$CO$_3$ and 903 mg (2.8 minol) of tetra-n-butylammonium bromide were added. 3-Hydroxybenzyl alcohol (3.48 g, 28 mmol) was added further, followed by stirring at room temperature for 5 days. The reaction mixture was concentrated under reduced pressure, followed by the addition of CHCl$_3$ and water to extract the reaction product into the organic layer. The extract was dried over Na$_2$SO$_4$ and then concentrated under reduced pressure. The residue was recrystallized from a CHCl$_3$-n-hexane mixed solvent, whereby 6.4 g of the title compound was obtained as pale yellow powder (yield: 93.1%).
Melting point: 92°–96° C.
$^1$H-NMR(CDCl$_3$)δ(ppm): 4.65(2H,s,—C$_6$H$_4$—CH$_2$—OH), 5.46(2H,s, C$_8$H$_5$N$_2$—CH$_2$—), 6.96(1H,d,J=7.8 Hz,—C$_6$H$_4$—), 6.99(1H,d,J=7.8 Hz,—C$_6$H$_4$), 7.11(1H,s,—C$_6$H$_4$—), 7.25(1H,dd,J=7.8,7.8 Hz,—C$_6$H$_4$—), 7.67(1H,dd, J=7.5,7.5 Hz,C $_8$H$_5$N$_2$—), 7.93(1H,dd,J=9.0,7.5 Hz,C$_8$H$_5$N$_2$), 7.95(1H,d,J=7.5 Hz,C$_8$H$_5$N$_2$—), 8.07(1H,d,J=9.0 Hz,C$_8$H$_5$N$_2$—), 9.43(1H,s,C$_8$H$_5$N$_2$—).
IR(KBr)cm$^{-1}$: 3328, 1621, 1613, 1582, 1441, 1378, 1292, 1077, 752.

EXAMPLE 33

Synthesis of 7[3-(2-quinazolinylmethoxyl)-benzyloxy]-3,4-dihydro-2H-1,4-benzothiazin-3-one To a solution of 1.00 g (3.76 mmol) of 3-(2-quinazolinylmethoxy)benzyl alcohol in 10 ml of CHCl$_3$, 0.5 ml of SOCl$_2$ was added, followed by stirring at room temperature for 15 hours. A small amount of MeOH was added to the reaction mixture and the solvents were distilled off under reduced pressure, whereby 1.08 g of 3-(2-quinazolinylmethoxy)benzyl chloride were obtained as white powder.

It was added to a solution of 567 mg (31.3 mmol) of 7-hydroxy-3,4-dihydro-2H-1,4-benzothiazin-3-one, followed by the further addition of 600 mg (47.0 mmol) of K$_2$CO$_3$ and 99.9 mg (3.1 mmol) of tetra-n-butylammonium bromide. The resultant mixture was stirred under an argon gas stream at room temperature for 7 days. The reaction mixture was concentrated under reduced pressure, and CHCl$_3$ and water were added to the residue to extract the reaction product into the organic layer. The extract was dried over Na$_2$SO$_4$ and then concentrated under reduced pressure. The residue was subjected to chromatography on a silica gel column. Subsequent to elution with CHCl$_3$, recrystallization was conducted from a CHCl$_3$-n-hexane mixed solvent, whereby 858 mg of the title compound was obtained as pale brown acicular crystals (yield: 53.2%).
Melting point: 167°–170° C.
$^1$H-NMR(CDCl$_3$)δ(ppm): 3.39(2H,s,—SCH$_2$CONH—), 4.99(2H,s,—C$_6$H$_4$—CH$_2$—), 5.47(2H,s,C$_8$H$_5$N$_2$—CH$_2$—), 6.67(1H,d,J=8.8 Hz,—C$_8$H$_6$NOS—), 6.74 (1H,dd,J=8.8,2.6 Hz,C$_8$H$_6$NOS—), 6.87(1H,d,J=2.6 Hz,C$_8$H$_6$NOS—), 6.89–6.99(2H,m,—C$_6$H$_4$—), 7.13(1H,s,—C$_6$H$_4$—), 7.28 (1H,dd,J=8.0,8.0 Hz,—C$_6$H$_4$—), 7.58–7.66(2H,m, C$_8$H$_5$N$_2$—,NH), 7.93 (1H,dd,J=9.0,7.5 Hz,C$_8$H$_5$N$_2$—), 7.95 (1H,d,J=7.8 Hz,C$_8$H$_5$N$_2$—), 8.07(1H,d,J=9.0 Hz,C$_8$H$_5$N$_2$—), 9.44(1H,s,C$_8$H$_5$N$_2$—).
IR(KBr)cm$^{-1}$: 2905, 1670, 1502, 1383, 1267, 1231, 1043, 834, 775, 749.

EXAMPLE 34

Synthesis of 7-[3-(2-quinazolinylmethoxy)benzyloxy]-1,2,3,4-tetrahydroquinolin-2-one In a similar manner as in Example 33, the title compound was obtained as yellow powder from 7-hydroxy-1,2,3,4-tetrahydroquinolin-2-one (yield: 31.1%).
Melting point: 178°–180° C. (acetone)
$^1$H-NMR(CDCl$_3$)δ(ppm): 2.53–2.67(2H,m,CH$_2$ at C3), 2.81–2.94(2H,m,CH$_2$ at C4), 5.00(2H,s,—C$_6$H$_4$—CH$_2$—), 5.48(2H,s,C$_8$H$_5$N$_2$—CH$_2$—), 6.34(1H,d,J=2.4 Hz,C8-H), 6.55(1H,dd,J=8.3,2.4 Hz,C6-H), 6.95–7.05(3H,m,Ar-H), 7.13–7.18(1H,m,Ar-H), 7.23–7.34(2H,m,Ar-H), 7.68(1H,td, J=8.0,1.2 Hz,Ar-H), 7.80(1H,brs,CONH), 7.90–8.00(2H,m, Ar-H), 8.08(1H,d,J=9.0 Hz,Ar-H), 9.45(1H,s,Ar-H).
IR(KBr)cm$^{-1}$: 1672, 1593, 1520, 1488, 1389, 1370, 1261, 1196, 1169, 1012, 785, 767.

EXAMPLE 35

Synthesis of 7-[4-(2-quinazolinylmethoxy)benzyloxy]-1,2,3,4-tetrahydroquinolin-2-one In a similar manner as in Example 33, the title compound was obtained as yellow prismatic crystals from 4-(2-quinazolinymethoxy)benzyl chloride and 7-hydroxy-1,2,3, 4-tetrahydroquinolin-2-one (yield: 38.6%).
Melting point: 178°–180° C. (acetone)
$^1$H-NMR(CDCl$_3$)δ(ppm): 2.52–2.66(2H,m,CH$_2$ at C3), 2.79–2.95(2H,m,CH$_2$ at C$_4$), 4.93(2H,s,—C$_6$H$_4$—CH$_2$—), 5.48(2H,s,C$_8$H$_5$N$_2$—CH$_2$—), 6.37(1H,d,J=2.4 Hz,C8-H), 6.58(1H,dd,J=8.3,2.4 Hz,C6-H), 6.94–7.14(3H,m,C$_6$H$_4$—), 7.32(2H,d,J=8.8 Hz,C$_6$H$_4$—), 7.60–7.73(1H,m,Ar-H), 7.87–8.00(3H,m,Ar-H,CONH), 8.08(1H,d,J=9.3 Hz,Ar-H), 9.45(1H,s,Ar-H).
IR(KBr)cm$^{-1}$: 1670, 1624, 1595, 1515, 1487, 1375, 1244, 1165, 1018.

PREPARATION EXAMPLE 5

Synthesis of 3-(N-methylbenzimidazol-2-ylmethoxy) benzyl alcohol

In a similar manner as in Preparation Example 4, the title compound was obtained as pale yellow acicular crystals from 2-chloromethyl-N-methylbenzimidazole (yield: 58.4%).
Melting point: 183°–185° C. (CHCl$_3$-n-hexane)
$^1$H-NMR(CDCl$_3$)δ(ppm): 3.81(3H,s,N—CH$_3$), 4.61(2H,s, —C$_6$H$_4$—CH$_2$—OH), 5.29(2H,s,C$_8$H$_7$N$_2$—CH$_2$—), 6.88–6.94(2H,m,—C$_6$H$_4$—), 7.02(1H,s,—C$_6$H$_4$—), 7.16–7.32(4H,m,Ar-H), 7.69(1H,m,C$_8$H$_7$N$_2$—).
IR(KBr)cm$^{-1}$: 2850, 1594, 1482, 1441, 1366, 1259, 1227, 1048, 1029, 750.

PREPARATION EXAMPLE 6

Synthesis of 4-(2-N-methylbenzimidazol-2-ylmethoxy) benzyl alcohol

In a similar manner as in Preparation Example 4, the title compound was obtained as pale yellow prismatic crystals from 2-chloromethyl-N-methylbenzimidazole and 4-hydroxybenzyl alcohol (yield: 58.4%).

Melting point: 176°–180° C. (CHCl$_3$-MeOH-n-hexane)

$^1$H-NMR(CDCl$_3$)δ(ppm): 3.88(3H,s,N—CH$_3$), 4.62(2H,s,—C$_6$H$_4$—CH$_2$—OH), 5.34(2H,s,C$_8$H$_7$N$_2$—CH$_2$—), 7.04 (2H,d,J=8.6 Hz,—C$_6$H$_4$—) 7.30(2H,d,J=8.6 Hz,—C$_6$H$_4$—), 7.23–7.38(3H,m,C$_8$H$_7$N$_2$—), 7.78(1H,m,C$_8$H$_7$N$_2$—).

IR(KBr)cm$^{-1}$: 3174, 2846, 1607, 1585, 1507, 1484, 1240, 1047, 1030, 743.

PREPARATION EXAMPLE 7

Synthesis of 3-(2-benzothiazolylmethoxy)benzyl alcohol

In a similar manner as in Preparation Example 4, the title compound was obtained as pale yellow acicular crystals from 2-chloromethylbenzothiazole (yield: 88.5%).

Melting point: 106°–108° C. (CHCl$_3$-n-hexane)

$^1$H-NMR(CDCl$_3$)δ(ppm): 1.86(1H,brt,OH), 4.69(2H,d,J=5.6 Hz,—C$_6$H$_4$—CH$_2$—OH), 5.48(2H,s,C$_7$H$_4$NS—CH$_2$—), 6.93–7.03(2H,m,Ar-H), 7.08(1H,br,Ar-H), 7.29(1H,dd,J=8.1,8.1 Hz,Ar-H), 7.40(1H,ddd,J=7.6,7.1,1.2 Hz,Ar-H), 7.50 (1H,ddd,J=7.6,7.1,1.2 Hz,Ar-H), 7.90(1H,d,J=7.6 Hz,Ar-H), 8.03(1H,d,J=7.6 Hz,Ar-H).

IR(KBr)cm$^{-1}$: 3322, 1596, 1439, 1365, 1264, 1207, 1156, 1062, 752.

PREPARATION EXAMPLE 8

Synthesis of 4-(2-benzothiazolylmethoxy)benzyl alcohol

In a similar manner as in Preparation Example 4, the title compound was obtained as colorless acicular crystals from 2-chloromethylbenzothiazole and 4-hydroxybenzylalcohol (yield: 89.8%).

Melting point: 137°–139° C. (CHCl$_3$-n-hexane)

$^1$H-NMR(CDCl$_3$)δ(ppm): 1.86(1H,overlapped with H$_2$O, OH), 4.63(2H,d,J=5.9 Hz,—C$_6$H$_4$—CH$_2$—OH), 5.50(2H,s, C$_7$H$_4$NS—CH$_2$—), 7.03(2H,dd,J=8.5,2.0 Hz,Ar-H), 7.32 (2H,dd,J=8.5,2.0 Hz,Ar-H), 7.40(1H,ddd,J=8.1,8.1,1.2 Hz,Ar-H), 7.50(1H,ddd,J=8.1,8.1,1.2 Hz,AR-H), 7.89(1H, dd,J=8.1,1.2 Hz,Ar-H), 8.03(1H,dd,J=8.1,1.2 Hz,Ar-H).

IR(KBr)cm$^{-1}$: 3364, 1612, 1585, 1522, 1512, 1361, 1252, 1056, 755.

PREPARATION EXAMPLE 9

Synthesis of 3-[N-(2-ethoxyethyl)benzimidazol-2-ylmethoxy]benzyl alcohol

In a similar manner as in Preparation Example 4, the title compound was obtained as colorless acicular crystals from 2-chloromethyl-N-(2-ethoxyethyl)benzimidazole (yield: 90.3%).

Melting point: 105°–107° C. (CHCl$_3$-n-hexane)

$^1$H-NMR(CDCl$_3$)δ(ppm): 1.10(3H,t,J=6.8 Hz,CH$_2$CH$_2$OCH$_2$CH$_3$), 2.24(1H,br,—C$_6$H$_4$—CH$_2$OH), 3.39(2H,q,J=6.8 Hz,CH$_2$CH$_2$OCH$_2$CH$_3$), 3.74(2H,t,J=5.4 Hz,—CH$_2$CH$_2$OCH$_2$CH$_3$), 4.48(2H,t,J=5.4 Hz,—CH$_2$CH$_2$OCH$_2$CH$_3$), 4.68(2H,d,J=5.6 Hz,—C$_6$H$_4$—CH$_2$—OH), 5.43(2H,s,C$_{11}$H$_{13}$N$_2$—CH$_2$O—), 6.96–7.62 (2H,m,—C$_6$H$_4$—), 7.11(1H,s,—C$_6$H$_4$—), 7.23–7.34 (3H,m,Ar-H), 7.41(1H,m,Ar-H), 7.71(1H,m,Ar-H).

IR(KBr)cm$^{-1}$: 2875, 1594, 1471, 1445, 1426, 1369, 1258, 1154, 1050, 1035, 761.

PREPARATION EXAMPLE 10

Synthesis of 4-[N-(2-ethoxyethylbenzimidazol-2-ylmethoxy]benzyl alcohol

In a similar manner as in Preparation Example 4, the title compound was obtained as pale yellow prismatic crystals from 2-chloromethyl-N-(ethoxyethyl)benzimidazole and 4-hydroxybenzyl alcohol (yield: 83.4%).

Melting point: 90°–92° C. (CHCl$_3$-n-hexane)

$^1$H-NMR(CDCl$_3$)δ(ppm): 1.10(3H,t, J=7.1 Hz,CH$_2$CH$_2$OCH$_2$CH$_3$), 1.66(1H,t,J=5.7 Hz,—C$_6$H$_4$—CH$_2$OH), 3.39(2H,q,J=7.1 Hz,CH$_2$CH$_2$OCH$_2$CH$_3$), 3.75 (2H,t,J=5.6 Hz,—CH$_2$CH$_2$OCH$_2$CH$_3$), 4.49(2H,t,J=5.6 Hz,—CH$_2$—CH$_2$OCH$_2$CH$_3$), 4.62(2H,d,J=5.7 Hz,—C$_6$H$_4$—CH$_2$—OH), 5.44(2H,s,C$_{11}$H$_{13}$N$_2$—CH$_2$O—), 7.08 (2H,d,J=8.8 Hz,—C$_6$H$_4$—), 7.25–7.34(4H,m,Ar-H), 7.41 (1H,m,Ar-H), 7.78(1H,m,Ar-H).

IR(KBr)cm$^{-1}$: 3180, 2858, 1609, 1587, 1509, 1472, 1417, 1237, 1117, 1036, 747.

EXAMPLES 36–46

Using the alcohol compounds obtained in Preparation Examples 5–10, the following compounds were obtained in a similar manner as in Example 33.

TABLE 3

| Ex. | Compound (1) | mp(°C.) |
|---|---|---|
| 36 | 7-[3-(N-methylbenzimidazol-2-yl methoxy)benzyloxy]-3,4-dihydro-2H-1,4-benzothiazin-3-one | 208–210 (dec) |
| 37 | 4-[3-(N-methylbenzimidazol-2-yl methoxy)benzyloxy]-3,3,7-trimethyl-2,3-hydro-1H-indol-2-one | 229–231 |
| 38 | 7-[4-(N-methylbenzimidazol-2-yl methoxy)benzyloxy]-3,4-dihydro-2H-1,4-benzothiazin-3-one | 203–207 (dec) |
| 39 | 4-[4-(N-methylbenzimidazol-2-yl methoxy)benzyloxy]-3,3,7-trimethyl-2,3-hydro-1H-indol-2-one | 207–211 (dec) |
| 40 | 7-[3-(2-benzothiazolylmethoxy)-benzyloxy]-3,4-dihydro-2H-1,4-benzothiazin-3-one | 185–187 (dec) |
| 41 | 7-[3-(2-benzothiazolylmethoxy)-benzyloxy]-1,2,3,4-tetrahydroquinolin-2-one | 180–181 |
| 42 | 7-[4-(2-benzothiazolylmethoxy)-benzyloxy]-1,2,3,4-tetrahydroquinolin-2-one | 199–201 |
| 43 | 4-[3-(N-ethoxyethylbenzimidazol-2-yl-methoxy)benzyloxy]-3,3,7-trimethyl-2,3-dihydro-1H-indol-2-one | 155–157 |
| 44 | 7-[3-(N-ethoxyethylbenzimidazol-2-yl-methoxy)benzyloxy]-3,4-dihydro-2H-1,4-benzothiazin-3-one | 122–125 |
| 45 | 4-[4-(N-ethoxyethylbenzimidazol-2 yl-methoxy)benzyloxy]-3,3,7-trimethyl-2,3-dihydro-1H-indol-2-one | 201–203 |
| 46 | 7-[4-(N-ethoxyethylbenzimidazol-2-yl-methoxy)benzyloxy]-3,4-dihydro-2H-1,4-benzothiazin-3-one | 170–173 (dec) |

EXAMPLE 47

Synthesis of 8-methyl-5-[3-(2-quinolinylmethoxy) benzyloxy]-3-(5-tetrazolyl)-1,2-dihydroquinolin-2-one A liquid mixture of 0.822 g (1.84 mmol) of the 3-cyano-8-methyl-5-[3-(2-quinolinylmethoxy)benzyloxy]-1,2-dihydroquinolin-2-one obtained in Example 3, 0.359 g (5.52 mmol) of NaN$_3$, 0.295 g (5.52 mmol) of NH$_4$Cl and 20 ml of DMF was stirred at a bath temperature of 120° C. for 8 hours. The solvent was distilled off and the residue was dissolved in a large amount of a CHCl$_3$—MeOH mixed solvent. The solution was washed with water and then dried over MgSO$_4$. The solvent was distilled off, whereby 0.519 g of the title compound was obtained as pale yellow powder (yield: 57.5%).

Melting point: 247°–248° C. (decomposed)

¹H-NMR(DMSO-d₆)δ(ppm): 2.39(3H,s,C8-CH₃), 5.27(2H, s,C₉H₆N—CH₂O), 5.39(2H,s,C₉H₆N—CH₂O), 6.80(1H,d, J=8.3 Hz,Ar-H), 7.04–7.16(2H,m,Ar-H), 7.22(1H,brs,Ar-H), 7.31–7.40(2H,m,Ar-H), 7.55–7.78(3H,m,Ar-H), 7.90–8.00(2H,m,Ar-H), 8.36(1H,d,J=8.3 Hz,Ar-H), 9.05 (1H,s,C4-H).
IR(KBr)cm⁻¹: 3056, 1655, 1611, 1492, 1298, 1240, 1103, 815.

EXAMPLE 48

Synthesis of 8-methyl-5-[4-(2-quinolinylmethoxy) benzyloxy]-3-(5-tetrazolyl)-1,2-dihydroquinolin-2-one Using the 3-cyano-8-methyl-5-[4-(2-quinolinylmethoxy) benzyloxy]-1,2-dihydroquinolin-2-one obtained in Example 19, the title compound was obtained as pale yellow powder in a similar manner as in Example 47 (yield: 26.4%).
Melting point: >300° C. (CHCl₃-n-hexane)
¹H-NMR(DMSO-d₆)δ(ppm): 5.26(2H,s,C₆H₄—CH₂O), 5.41(2H,s,C₉H₆N—CH₂O), 6.85–6.94(1H,br,Ar-H), 7.14 (1H,d,J=8.5 Hz,Ar-H), 7.20–7.35(1H,m,Ar-H), 7.48(2H,m, Ar-H), 7.54–7.65(2H,m,Ar-H), 7.70(1H,d,J=8.5 Hz,Ar-H), 7.73–7.90(1H,m,Ar-H), 8.02(2H,t,J=8.8 Hz,Ar-H), 8.42 (1H,d,Ar-H), 9.20(1H,brs,CONH).
IR(KBr)cm⁻¹: 3403, 1659(CONH), 1612, 1519, 1240, 1092, 823.

EXAMPLE 49

Synthesis of 4-[3-(2-quinolinylmethoxy)benzyloxy]-3,3,7-trimethyl-2,3-dihydro-1H-indol-2-thione To 1.189 g (2.71 mmol) of the 4-[3-(2-quinolinylmethoxy)benzyloxy]-3,3,7-trimethyl-2,3-dihydro-1H-indol-2-one obtained in Example 13, 1.076 g (2.71 mmol) of the Lawesson's reagent and 10 ml of toluene were added, followed by stirring at a bath temperature of 100° C. for 3 hours. After CHCl₃ was added to dissolve the insoluble matter, the resulting solution was subjected to chromatography on a silica gel column. Subsequent to elution with CHCl₃, recrystallization was conducted from AcOEt, whereby 678 mg of the title compound were obtained as pale yellow powder (yield: 55.0%).
Melting point: 174°–176° C. (decomposed)
¹H-NMR(DMSO-d₆)δ(ppm): 1.51(6H,s,C3-CH₃×2), 2.27 (3H,s,C7—CH₃), 5.07(2H,s,C₆H₄-CH₂O—), 5.41(2H,s, C₉H₆N—CH₂O), 6.57(1H,d,J=8.3 Hz,C5-H), 6.82–7.12 (5H,m,Ar-H), 7.22–7.38(1H,m,Ar-H), 7.48–7.90(5H,m,Ar-H), 8.10(1H,d,J=8.3 Hz,Ar-H), 8.19(1H,d,J=8.8 Hz,Ar-H), 10.03(1H,s,CSNH).
IR(KBr)cm⁻¹: 3122, 3069, 2973, 2906, 1605, 1586, 1509, 1478, 1451, 1441, 1370, 1288, 1267, 1178, 1152, 1083, 1065, 819, 788, 781, 738, 688.

EXAMPLE 50

Synthesis of 2-oxo-6-[3-(2-quinolinylmethoxy) benzyloxy]-1,2-dihydroquinoline-3-carboxylic acid To a solution of 255 mg (0.588 mmol) of the 3-cyano-6-[3-(2-qinolinylmethoxy)benzyloxy]-1,2-dihydroquinolin-2-one in 10 ml of EtOH, 10 ml of a 50% aqueous NaOH solution were added, followed by stirring at room temperature for 6 hours. Water was added to the reaction mixture. After the thus-obtained mixture was acidified with concentrated HCl, the precipitate was collected by filtration. Subsequent to washing with water, the precipitate was dried in air and then recrystallized from a CHCl₃—MeOH-ethyl ether mixed solvent, whereby 120 mg of the title compound were obtained as yellow powder (yield: 45.1%).
Melting point: 282°–285° C. (decomposed)
¹H-NMR(CD₃OD)δ(ppm): 5.64(2H,s,—C₆H₄—CH₂—), 5.68(2H,s,C₉H₆N—CH₂—), 6.87(1H,s,Ar-H), 7.00–7.45 (6H,m,Ar-H), 8.03(1H,d,J=8.0 Hz,Ar-H), 8.10–8.29(3H,m, Ar-H), 9.01(1H,d,J=8.5 Hz,Ar-H).
IR(KBr)cm⁻¹: 3421, 1644, 1584, 1450, 1396, 1244, 1154, 821.

EXAMPLE 51

Synthesis of 8-methyl-2-oxo-5-[3-(2-quinolinylmethoxy) benzyloxy]- 1,2-dihydroquinoline-3-carboxylic acid Using 3-cyano-8-methyl-5-[3-(2-quinolinylmethoxy) benzyloxy]-1,2-dihydroquinolin-2-one obtained in Example 3, the title compound was obtained as pale yellow powder in a similar manner as in Example 5 (yield: 78.3%).
Melting point: 237°–239° C. (CHCl₃—MeOH)
¹H-NMR(DMSO-d₆)δ(ppm): 2.39(3H,s,C8-CH₃), 5.26(2H, s,—C₆H₄—CH₂O), 5.39(2H,s,C₉H₆N—CH₂O), 6.87(1H,d, J=8.8 Hz,C7-H), 7.03–7.16(2H,m,Ar-H), 7.19(1H,s,C₆H₄), 7.36(1H,t,J=8.0 Hz,C₆H₄), 7.47(1H,d,J=8.8 Hz,Ar-H), 7.57–7.67(2H,m,Ar-H), 7.70–7.80(1H,m,Ar-H), 7.97(2H,d, J=8.0 Hz,C₆H₄), 8.36(1H,d,J=8.8 Hz,C6-H), 8.98(1H,s, C₄—H), 12.25(1H,brs,CONH), 14.71(1H,brs,COOH).
IR(KBr)cm⁻¹: 2800–2300(COOH), 1742(COOH), 1621 (CONH), 1497, 1438, 1276, 1261, 1087.

EXAMPLE 52

Synthesis of 8-methyl-2-oxo-5-[4-(2-quinolinylmethoxy) benzyloxy]-1,2-dihydroquinoline-3-carboxylic acid Using 3-cyano-8-methyl-5-[4-(2-quinolinylmethoxy) benzyloxy]-1,2-dihydroquinolin-2-one obtained in Example 19, the title compound was obtained as pale yellow powder in a similar manner as in Example 50 (yield: 62.9%).
Melting point: 260°–261° C. (decomposed)
¹H-NMR(DMSO-d₆)δ(ppm) : 2.41(3H,s,C8-CH₃), 5.20(2H, s,C₆H₄—CH₂O), 5.40(2H,s,C₉H₆N—CH₂O), 6.97(1H,d,J= 8.3 Hz,Ar-H), 7.13(2H,d,J=8.8 Hz,Ar-H), 7.42–7.84(6H,m, Ar-H), 7.95–8.08(2H,m,Ar-H), 8.43(1H,d,J=8.3 Hz,Ar-H), 8.96(1H,s,C4-H), 12.30(1H,brs,CONH), 14.70(1H,brs, COOH).
IR(KBr)cm⁻¹: 2800–2300(COOH), 1753(COOH), 1624 (CONH), 1495, 1433, 1252, 1240, 1082, 870, 830, 805.

EXAMPLE 53

Synthesis of 3-cyano-8-methyl-5-[3-(2-quinolinylmethoxy)benzoyloxy]-1,2-dihydroquinolin-2-one A liquid mixture of 0.838 g (3 mmol) of 3-(2-quinolinylmethoxy)benzoic acid, 0.601 g (3 mmol) of 3-cyano-5-hydroxy-8-methylcarbostyryl, 50 ml of DMF, 0.931 g (6 mmol) of WSC.HCl and 0.73 g (0.6 mmol) of 4-dimethylaminopyridine was stirred under an argon gas stream at a bath temperature of 50° C. for 2 days. The solvent was distilled off from the reaction mixture under reduced pressure. Water was added to the residue, and the resulting mixture was extracted with a 2:1 mixed solvent of CHCl₃ and MeOH. The extract was washed with water, dried over MgSO₄ and then concentrated. The concentrate was allowed to stand overnight, whereby 0.495 g of the title compound was obtained as yellow powder (yield: 35.8%).
Melting point: 257°–260° C. (decomposed)
¹H-NMR(DMSO-d₆)δ(ppm): 2.46(3H,s,CH₃), 5.51(2H,s, CH₂O—C₆H₄), 7.14(1H,d,J=7.8 Hz,Ar-H), 7.42–7.91(8H, m,Ar-H), 8.01(2H,d,J=8.8 Hz,Ar-H), 8.44(1H,d,J=8.3 Hz,AR-H), 8.83(1H,s,C4-H), 11.80(1H,brs,CONH).
IR(KBr)cm⁻¹: 3174, 3047, 2230(CN), 1754(COO), 1660 (CONH), 1618, 1585, 1491, 1278, 1238, 1200, 1074, 1043, 740.

EXAMPLES 54–69

The following compounds were obtained in a similar manner as in Example 53.

TABLE 4

| Ex. | Compound (1) | mp(°C.) |
|---|---|---|
| 54 | 8-Methyl-5-[3-(2-quinolinylmethoxy)-benzoyloxy]-1,2,3,4-tetrahydro-quinolin-2-one | 162–164 |
| 55 | 6-[3-(2-Quinolinylmethoxy)benzoyloxy]-1,2,3,4-tetrahydroquinolin-2-one | 215–217 |
| 56 | 7-[3-(2-Quinolinylmethoxy)benzoyloxy]-1,2,3,4-tetrahydroquinolin-2-one | 177–179 |
| 57 | 7-[3-(2-Quinolinylmethoxy)benzoyloxy-2,3,4,5-tetrahydro-1H-benzo[b]azepin-2-one | 175–177 |
| 58 | 7-[3-(2-Quinolinylmethoxy)benzoyloxy]-3,4-dihydro-2H-1,4-benzothiazin-3-one | 217–219 (dec) |
| 59 | 3,3-Dimethyl-5-[3-(2-quinolinylmethoxy)benzoyloxy]-2,3-dihydro-1H-indol-2-one | 224–226 (dec) |
| 60 | 3,3-Dimethyl-6-[3-(2-quinolinylmethoxy)benzoyloxy]-2,3-dihydro-1H-indol-2-one | 180–184 (dec) |
| 61 | 3,3-Dimethyl-7-[3-(2-quinolinylmethoxy)benzoyloxy]-2,3-dihydro-1H-indol-2-one | 221–224 (dec) |
| 62 | 3-Cyano-8-methyl-5-[4-(2-quinolinylmethoxy)benzoyloxy]-1,2-dihydro-quinolin-2-one | 277–278 (dec) |
| 63 | 8-Methyl-5-[4-(2-quinolinylmethoxy)-benzoyloxy]-1,2,3,4-tetrahydro-quinolin-2-one | 200–202 |
| 64 | 6-[4-(2-Quinolinylmethoxy)benzoyloxy]-1,2,3,4-tetrahydroquinolin-2-one | 248–250 (dec) |
| 65 | 7-[4-(2-Quinolinylmethoxy)benzoyloxy]-1,2,3,4-tetrahydroquinolin-2-one | 244–246 (dec) |
| 66 | 7-[4-(2-Quinolinylmethoxy)benzoyloxy]-3,4-dihydro-2H-1,4-benzothiazin-3-one | 240–243 (dec) |
| 67 | 3,3-Dimethyl-5-[4-(2-quinolinylmethoxy)benzoyloxy]-2,3-dihydro-1H-indol-2-one | 227–230 (dec) |
| 68 | 3,3-Dimethyl-6-[4-(2-quinolinylmethoxy)benzoyloxy]-2,3-dihydro-1H-indol-2-one | 211–215 (dec) |
| 69 | 3,3-Dimethyl-7-[4-(2-quinolinylmethoxy)benzoyloxy]-2,3-dihydro-1H-indol-2-one | 193–196 (dec) |

EXAMPLES 70–73

Using 8-amino-3,4-dihydro-2H-1,4-benzothiazin-3-one or 7-amino-3,4-dihydro-2H-1,4-benzothiazin-3-one, the following compounds were obtained in a similar manner as in Example 53.

TABLE 5

| Ex. | Compound (1) | mp(°C.) |
|---|---|---|
| 70 | 8-[3-(2-Quinolinylmethoxy)benzoyl-amino]-3,4-dihydro-2H-1,4-benzo-thiazin-3-one | 235–238 (dec) |
| 71 | 8-[4-(2-Quinolinylmethoxy)benzoyl-amino]-3,4-dihydro-2H-1,4-benzo-thiazin-3-one | 277–279 (dec) |
| 72 | 7-[3-(2-Quinolinylmethoxy)benzoyl-amino]-3,4-dihydro-2H-1,4-benzo-thiazin-3-one | 240–242 (dec) |
| 73 | 7-[4-(2-Quinolinylmethoxy)benzoyl-amino]-3,4-dihydro-2H-1,4-benzo-thiazin-3-one | 258–260 (dec) |

EXAMPLE 74

Synthesis of 7-[3-(2-quinolinylmethoxy)benzyloxy]-3,4-dihydro-2H-1,4-benzothiazin-3-one 1,1-dioxide 7-[3-(2-Quinolinylmethoxy)benzyloxy]-3,4-dihydro-2H-1,4-benzothiazin-3-one (0.639 g, 1.49 mmol) obtained in Example 10 was dissolved in 90 ml of $CHCl_3$, to which a solution of 1.04 g (3 mmol) of m—CPBA (metachloroperbenzoic acid) in 30 ml of $CHCl_3$ was added at room temperature. The resultant mixture was stirred for 72 hours. The reaction mixture was washed successively with a saturated aqueous solution of $NaHCO_3$ and water in this order, dried over magnesium sulfate and then concentrated, whereby 0.219 g of the title compound was obtained as pale yellow powder (yield: 31.9%).

Melting point: 233°–234° C. (decomposed)

$^1$H-NMR(DMSO-$d_6$)δ(ppm): 4.68(2H,s,$CH_2$ at C2), 5.19 (2H,s,$C_6H_4$—$CH_2O$—), 5.49(2H,s,$C_9H_6N$—$CH_2$—), 7.00–7.42(6H,m,Ar-H), 7.58–7.92(4H,m,Ar-H), 8.02(1H,d, J=8.8 Hz,Ar-H), 8.13(1H,d,J=8.8 Hz,Ar-H), 8.61(1H,d,J= 8.8 Hz,Ar-H), 11.08(1H,s,CONH).

IR(KBr)$cm^{-1}$: 1702(CONH), 1494, 1326, 1309($SO_2$), 1253, 1237, 1223, 1138($SO_2$).

EXAMPLES 75–80

Using the compounds obtained in Examples 11, 32, 33, 36, 40 an 72, the following compounds were obtained similar manner as in Example 74.

TABLE 6

| Ex. | Compound (1) | mp (°C.) |
|---|---|---|
| 75 | 7-[3-(7-Chloro-2-quinolinylmethoxy)-benzyloxy]-3,4-dihydro-2H-1,4-benzo-thiazin-2-one 1,1-dioxide | 229–231 (dec) |
| 76 | 8-[3-(2-Quinolinylmethoxy)benzyloxy]-2,3,4,5-tetrahydro-1,5-benzo-thiazepin-4-one 1,1-dioxide | 221–223 (dec) |
| 77 | 7-[3-(2-Quinolinylmethoxy)benzyloxy]-3,4-dihydro-2H-1,4-benzothiazin-3-one 1,1-dioxide | 227–229 (dec) |
| 78 | 7-[3-(2-Benzothiazolylmethoxy)benzyl-oxy]-3,4-dihydro-2H-1,4-benzothiazin-3-one 1,1-dioxide | 198–200 (dec) |
| 79 | 7-[3-(N-Methylbenzimidazol-2-yl-methoxy)benzyloxy]-3,4-dihydro-2H-1,4-benzothiazin-3-one 1,1-dioxide | 144–149 |
| 80 | 7-[3-(2-Quinolinylmethoxy)benzoyl-amino-3,4-dihydro-2H-1,4-benzo-thiazin-3-one 1,1-dioxide | 244–250 (dec) |

EXAMPLE 81

Synthesis of trans-7-[3-[2-(7-chloroquinolin-2-yl)ethenyl]benzyloxy]-2H-3,4-dihydro-1,4-benzothiazin-3-one 1) Synthesis of 7-chloro-2-quinolylmethyl(triphenyl)phosphilic chloride 7-Chloro-2-chloromethylquinoline (4.81 g, 22.7 mmol) was dissolved in 100 ml of toluene, followed by the addition of 7.74 g (22.7 mmol) of triphenylphosphine. The resultant mixture was heated under reflux for 24 hours. After the reaction mixture was concentrated, insoluble matter was collected by filtration and then washed with ethyl ether, whereby 8.54 g of the title compound were obtained as gray powder (yield: 79.3%).

$^1$H-NMR($CDCl_3$)δ(ppm): 6.09(2H,d,J=14.4 Hz,—$CH_2$P—), 7.43(1H,dd,J=8.6,2.0 Hz,Ar-H), 7.49(1H,d,J=2.0 Hz,Ar-H), 7.54–7.79(10H,m,Ar-H), 7.86–7.98(6H,m,Ar-H), 8.05 (1H,d,J=8.6 Hz,Ar-H), 8.25(1H,d,J=8.5 Hz,Ar-H).

2) Synthesis of 3-[2-{2-(7-chloro)quinolyl}]ethenylbenzaldehyde

7-Chloro-2-quinolylmethyl(triphenyl)phosphilic chloride (4.60 g, 9.70 mmol) was dissolved in 100 ml of dry THF, to which a solution of 1.09 g (9.70 mmol) of t-BuOK in 50 ml of dry THF was added dropwise under an $N_2$ gas stream. The resultant mixture was stirred at room temperature for 10 minutes. To the solution, a solution of 1.30 g (9.70 mmol) of isophthalaldehyde in 30 ml of dry THF was added dropwise. The resultant mixture was stirred at room temperature for 2 hours. Water (300 ml) was added to the reaction mixture, followed by the extraction of the organic layer with $CHCl_3$. The extract was dried over anhydrous $Na_2SO_4$, the solvent was distilled off and the residue was then recrystallized from a $CHCl_3$-MeOH-n-hexane mixed solvent, whereby 4.46 g of the title compound were obtained as pale yellow powder (a 6:94 mixture of the cis-form and the trans-form) (yield: 91.9%).

Melting point: 105°–107° C.

$^1$H-NMR($CDCl_3$)δ(ppm): 7.40–7.92(9H,m,Ar-H) , 8.07–8.18(2H,m,Ar-H), 10.08(1H(94%),s,CHO(trans)), 10.13(1H,(6%),s,CHO(cis)).

IR(KBr)cm$^{-1}$: 1688, 1591, 1439, 1190, 1122, 973, 721, 542.

3) Synthesis of trans-3-[2-(7-chloro)quinolin-2-yl)ethenyl]benzyl alcohol

3-[2-(7-Chloroquinolin-2-yl)ethenyl]benzaldehyde (cis/trans=6:94) (2.53 g, 7.28 mmol) was suspended in 160 ml of MeOH, followed by the addition of 182 mg (10.4 mmol) of $NaBH_4$. The resultant mixture was then stirred at room temperature for 24 hours. Insoluble matter was filtered off from the reaction mixture and then washed with $CHCl_3$. The filtrate and the washing were combined together, from which the solvent was distilled off under reduced pressure. The residue was subjected to chromatography on a silica gel column. Subsequent to elution with $CHCl_3$, recrystallization was conducted from a $CHCl_3$-n-hexane mixed solvent, whereby 1.25 g of the title compound were obtained as pale yellow leaflet crystals (yield: 58.1%).

Melting point: 138°–140° C.

$^1$H-NMR($CDCl_3$)δ(ppm): 7.31–7.48(4H,m,Ar-H and vinyl-H), 7.56(1H,d,J=7.6 Hz,Ar-H), 7.63(1H,d,J=8.5 Hz,Ar-H), 7.65(1H,s,Ar-H), 7.71(1H,d,J=8.8 Hz,Ar-H), 7.71(1H,d,J=13.7 Hz,vinyl-H), 8.05–8.13(2H,m,Ar-H).

IR(KBr)cm$^{-1}$: 1607, 1591, 1497, 1409, 1040, 974, 840, 697.

4) Synthesis of trans-3-[2-(7-chloroquinolin-2-yl)ethenyl]benzyloxy]-3,4-dihydro-2H-1,4-benzothiazin-3-one To a solution of 813 mg (2.75 mmol) of trans-3-[2-(7-chloroquinolin-2-yl)ethenyl]benzyl alcohol in 40 ml of $CHCl_3$, 1.0 ml of $SOCl_2$ was added, followed by stirring at room temperature for 24 hours. A small amount of MeOH was added to the reaction mixture and the solvent was distilled off under reduced pressure, whereby trans-3-[2-(7-chloroquinolin-2-yl)ethenyl]-benzyl chloride was obtained as pale yellow powder.

It was added to a solution of 415 mg (2.29 mmol) of 7-hydroxy-3,4-dihydro-2H-(1,4)-benzothiazin-3-one in 70 ml of DMF, followed by the addition of 475 mg (3.44 mmol) of $K_2CO_3$ and 31.8 mg (0.23 mmol) of tetra-n-butylammonium bromide. The resultant mixture was stirred under an argon gas stream at 100° C. for 16 hours. The reaction mixture was concentrated under reduced pressure, and $CHCl_3$ and water were added to the residue to extract the reaction product into the organic layer. The extract was dried over $Na_2SO_4$ and then concentrated under reduced pressure. The residue was subjected to chromatography on a silica gel column. Subsequent to elution with $CHCl_3$, recrystallization was conducted from a $CHCl_3$-n-hexane mixed solvent, whereby 193 mg of the title compound were obtained as pale yellow powder (yield: 18.4%).

Melting point: 205°–208° C. (decomposed)

$^1$H-NMR($CDCl_3$)δ(ppm): 3.42(2H,s,—$SCH_2$CONH—), 5.07(2H,s,—$C_6H_4$—$CH_2$—), 6.78(1H,d,J=8.8 Hz,C5-H), 6.83(1H,dd,J=8.8,2.7 Hz,C6-H), 6.97(1H,d,J=2.7 Hz,C8-H), 7.35–7.48(4H,m,Ar-H and vinyl-H), 7.59–7.78(5H,m, Ar-H and vinyl-H), 8.02(1H,br,NH), 8.02–8.13(2H,m,Ar-H).

IR(KBr)cm$^{-1}$: 1668, 1608, 1592, 1497, 1377, 1223, 1068, 834, 692.

EXAMPLE 82

Synthesis of 7-[3-(2-quinazolinylmethoxy)benzyloxy]-2,3,4,5-tetrahydro-1H-benz[b]azepin-2-one The title compound was obtained in a similar manner as in Example 33 (yield: 15.3%).

Melting point: 128°–131° C.

EXAMPLE 83

Synthesis of 7-[3-(1-methylbenzimidazol-2-yl)-benzyloxy]-2,3,4,5-tetrahydro-1H-benz[b]azepin-2-one Using the alcohol compound obtained in Preparation Example 5, the title compound was obtained in a similar manner as in Example 33 (yield: 23.3%).

Melting point: 159°–162° C.

EXAMPLE 84

Synthesis of 7-[3-(2-quinolinylmethoxy)benzyloxy]-2,3,4,5-tetrahydro-1H-benz[c]azepin-1-one The title compound was obtained in a similar manner as in Example 1 (yield: 79.3%).

Melting point: 172°–173° C.

EXAMPLE 85

Synthesis of 7-[4-(2-quinolinylmethoxy)-benzyloxy]-2,3,4,5-tetrahydro-1H-benz[c]azepin-1-one The title compound was obtained in a similar manner as in Example 18 (yield: 63.7%).

Melting point: 181°–183° C.

EXAMPLE 86

Synthesis of 7-[3-(2-quinazolinylmethoxy)benzyloxy]-2,3,4,5-tetrahydro-1H-benz[c]azepin-1-one The title compound was obtained in a similar manner as in Example 33 (yield: 28.4%).

Melting point: 172°–173° C.

EXAMPLE 87

Synthesis of 7-[3-(2-quinolinylmethoxy)benzyloxy]-2,3,4,5-tetrahydro-tetrazolo[5,1-a][2]benzazepin The title compound was obtained in a similar manner as in Example 1 (yield: 54.8%).

Melting point: 136°–138° C.

EXAMPLE 88

Synthesis of 7-[4-(2-quinolinylmethoxy)benzyloxy]-2,3,4,5-tetrahydro-tetrazolo-[5,1-a][2]benzazepin The title compound was obtained in a similar manner as in Example 18 (yield: 17.9%).

Melting point: 217°–219° C.

EXAMPLE 89

Synthesis of 6-[3-(2-quinolinylmethoxy)benzyloxy]-1-tetralone

The title compound was obtained in a similar manner as in Example 1 (yield: 36.5%).
Melting point: 93° C.

EXAMPLE 90

Synthesis of 6-[3-(2-quinazolinylmethoxy)benzyloxy]-1-tetralone

The title compound was obtained in a similar manner as in Example 33 (yield: 7.4%).
Melting point: 97°–98° C.

EXAMPLE 91

Synthesis of 7-[3-(2-quinolinylmethoxy) benzylidenamino]-3,4-dihydro-2H-1,4-benzothiazin-3-one A liquid mixture of 1.316 g (5 mmol) of 3-(2-quinolinylmethoxy)benzaldehyde, 0.901 g (5 mmol) of 7-amino-3,4-dihydro-2H-1,4-benzothiazin-3-one and 70 ml of EtOH was heated under reflux and stirring for 24 hours. The mixture was then allowed to cool down. The precipitate was collected by filtration, whereby 1.969 g of the title compound were obtained as pale yellow powder (yield: 92.3%).
Melting point: 209°–210° C. (decomposed)
$^1$H-NMR(DMSO-d$_6$)δ(ppm): 3.50(2H,s,CH$_2$ at C2), 5.45 (2H,s,C$_9$H$_6$NCH$_2$O), 7.01(1H,d,J=8.8 Hz,Ar-H), 7.08–7.87 (9H,m,Ar-H), 8.02(2H,t,J=8.3 Hz,Ar-H), 8.43(1H,d,J=8.3 Hz,Ar-H), 8.63(1H,s,—CH=N—), 10.65(1H,s,CONH).
IR(KBr)cm$^{-1}$: 3183, 1679, 1624, 1598, 1584, 1492, 1371, 1267, 1255, 1202, 826, 816, 783.

EXAMPLE 92

Synthesis of 7-[4-(2-quinolinylmethoxy) benzylidenamino]-3,4-dihydro-2H-1,4-benzothiazin-3-one The title compound was obtained in a similar manner as in Example 91 (yield: 96.1%).
Melting point: 277°–279° C. (decomposed)

EXAMPLE 93

Synthesis of 8-[3-(2-quinolinylmethoxy) benzylidenamino]-3,4-dihydro-2H-1,4-benzothiazin-3-one The title compound was obtained in a similar manner as in Example 91 (yield: 93.3%).
Melting point: 170°–173° C. (decomposed)

EXAMPLE 94

Synthesis of 7-[3-(2-quinolinylmethoxy)benzylamino]-3,4-dihydro-2H-1,4-benzothiazin-3-one 7-[3-(2-Quinolinylmethoxy)benzylidenamino]-3,4-dihydro-2H-1,4-benzothiazin-3-one (6.383 g, 15 mmol) obtained in Example 91 was dissolved in a mixed solvent consisting of 200 ml of DMF and 50 ml of MeOH, followed by the addition of 2.26 g (60 mmol) of NaBH$_4$ in small portions. After the resultant mixture was stirred for 30 minutes at room temperature, the solvent was distilled off under reduced pressure. Water was added to the residue, followed by extraction with CHCl$_3$. The extract was washed with water, dried over MgSO$_4$ and then concentrated. The concentrate was recrystallized from MeOH-AcOEt, whereby 5.117 g of the title compound were obtained as white powder (yield: 79.8%).
Melting point: 147°–149° C.
$^1$H-NMR(DMSO-d$_6$)δ(ppm): 3.34(2H,s,CH,at C2), 4.20 (2H,d,J=5.9 Hz, —CH$_2$NH—), 5.34(2H,s,C$_9$H$_6$NCH$_2$O), 6.18(1H,t,J=5.9 Hz,NH), 6.32–6.50(2H,m,Ar-H), 6.68(1H, d,J=8.8 Hz,Ar-H), 6.82–7.00(2H,m,Ar-H), 7.07 (1H,s,Ar-H), 7.24(1H,t,J=7.8 Hz,Ar-H), 7.55–8.07(5H,m,Ar-H), 8.40 (1H,d,J=8.8 Hz,Ar-H), 10.13(1H,s,CONH).
IR(KBr)cm$^{-1}$: 3430, 1663, 1613, 1600, 1505, 1263, 1251, 1157, 823, 792, 780.

EXAMPLE 95

Synthesis of 8-[3-(2-quinolinylmethoxy)benzylamino]-3,4-dihydro-2H-1,4-benzothiazin-3-one The title compound was obtained in a similar manner as in Example 94 (yield: 81.3%).
Melting point: 179°–181° C.

EXAMPLE 96

Syntheses of 7-[N-methyl-N-{3-(2-quinolinylmethoxy) benzyl}amino]-3,4-dihydro-2H-1,4-benzothiazin-3-one (a) and 4-methyl-7-[N-methyl-N-{3-(2-quinolinylmethoxy) benzyl}amino]-3,4-dihydro-2H-1,4-benzothiazin-3-one (b)

After a mixture of 2.147 g (5.02 mmol) of 1,4-benzothiazin-3-one, 0.852 g (6 mmol) of CH$_3$I, 1.658 g (12 mmol) of K$_2$CO$_3$, 0.161 g (0.5 mmol) of (n-Bu)$_4$NBr and 60 ml of DMF was stirred at room temperature for 3 days, the solvent was distilled off under reduced pressure. Water was added to the residue, followed by extraction with CHCl$_3$. The extract was washed with water, dried over MgSO$_4$ and then concentrated. The residue was subjected to chromatography on a silica gel column. Subsequent to elution with CHCl$_3$, the first eluate was recrystallized from AcOEt, whereby 0.091 g of the title compound (b) was obtained (yield: 4.0%). Subsequently, the second eluate was recrystallized from CHCl$_3$—MeOH, whereby 0.500 g of the title compound (a) was obtained as colorless foliaceous crystals (yield: 22.6%).

Title compound (a)
Melting point: 196°–198° C. (decomposed)
$^1$H-NMR(CDCl$_3$)δ(ppm): 2.96(3H,s,CH$_3$—N—C7), 3.39 (2H,s,CH$_2$ at C2), 4.44(2H,S,—CH$_2$N(Me)—), 5.35(2H,s, C$_9$H$_6$NCH$_2$O), 6.47(1H,dd,J=2.8,8.8 Hz,C6-H), 6.60(1H,d, J=2.8 Hz,C8-H), 6.61(1H,d,J=8.8 Hz,C5-H), 6.77–6.97(3H, m,Ar-H), 7.24(1H,t,J=7.8 Hz,Ar-H), 7.56(1H,t,J=6.8 Hz,Ar-H), 7.64(1H,d,J=8.8 Hz,Ar-H), 7.70–7.78(1H,m,Ar-H), 7.83 (1H,d,J=8.3 Hz,Ar-H), 7.93(1H,br.s,CONH), 8.07(1H,d,J= 8.3 Hz,Ar-H), 8.18(1H,d,J=8.8 Hz,Ar-H).
IR(KBr)cm$^{-1}$: 1666, 1610, 1510, 1373, 1286, 1069, 783.

Title compound (b)
Melting point: 108°–110° C.
$^1$H-NMR(CDCl$_3$)δ(ppM): 2.97(3H,s,CH$_3$—N—C7), 3.37 (3H,s,N4—CH$_3$), 3.38(2H,s,CH$_2$ at C2), 4.46(2H,S,— CH$_2$N(Me)—), 5.35(2H,s,C$_9$H$_6$NCH$_2$O), 6.55(1H,dd,J=2.9, 8.8 Hz,C6-H), 6.66(1H,d,J=2.9 Hz,C8-H), 6.78–6.95(4H,m, Ar-H), 7.25(1H,t,J=7.8 Hz,Ar-H), 7.52–7.60(1H,m,Ar-H), 7.65(1H,d,J=8.8 Hz,Ar-H), 7.69–7.86(2H,m,Ar-H), 8.06 (1H,d,J=8.3 Hz,Ar-H), 8.18(1H,d,J=8.8 Hz,Ar-H).
IR(KBr)cm$^{-1}$: 1652, 1608, 1582, 1509, 1373, 1286, 1253, 1141, 1060, 827, 782, 748.

EXAMPLE 97

Synthesis of 4-methyl-8-[3-(2-quinolinylmethoxy) benzylamino]-3,4-dihydro-2H-1,4-benzothiazin-3-one After a mixture of 1.690 g (3.95 m-mol) of 8-[3-(2-quinolinylmethoxy)benzylamino]-3,4-dihydro-2H-1,4-benzothiazin-3-one obtained in Example 95, 0.673 g (4.74 mmol) of CH$_3$I, 1.311 g (9.5 mmol) of K$_2$CO$_3$, 0.129 g (0.4 mmol) of (n-Bu)$_4$NBr and 50 ml of DMF was stirred at room temperature for 3 days, the solvent was distilled off under reduced pressure. Water was added to the residue, followed by extraction with CHCl₃. The extract was washed with water, dried over MgSO₄ and then concentrated. The residue was subjected to chromatography on a silica gel column. Subsequent to elution with CHCl₃, recrystallization was conducted from an acetone-n-hexane mixed solvent, whereby 1.000 g of the title compound was obtained (yield: 57.3%).

Melting point: 102°–104° C.

$^1$H-NMR(CDCl$_3$)δ(ppm): 3.32(2H,s,CH$_2$ at C2), 3.41(3H,s, N—CH$_3$), 4.37(2H,d,J=5.4 Hz,C$_8$NHCH$_2$), 4.55(1H,t,J=5.4 Hz,C8-NH), 5.38(2H,s,C$_9$H$_6$NCH$_2$O), 6.34(1H,d,J=8.3 Hz,Ar-H), 6.47(1H,d,J=7.8 Hz,Ar-H), 6.91–7.08(4H,m,Ar-H), 7.24–7.32(1H,m,Ar-H), 7.51–7.59(1H,m,Ar-H), 7.64 (1H,d,J=8.3 Hz,Ar-H), 7.70–7.77(1H,m,Ar-H), 7.82(1H,d, J=7.8 Hz,Ar-H), 8.06(1H,d,J=9.3 Hz,Ar-H), 8.17(1H,d,J= 8.3 Hz,Ar-H).

IR(KBr)cm$^{-1}$: 3371, 2965, 1659, 1589, 1470, 1359, 1285, 1252, 1076, 819, 768, 742.

Test 1

Antihistaminic Action and Anti-LTD₄ Action (In vitro Tests)

An isolated guinea pig ileum was cut into about 2 cm lengths. Each ileum piece was suspended in a 20-ml container filled with the Krebs buffer. An isotonic contractive response by histamine or leukotriene D₄ was recorded on a recorder. The Krebs buffer was controlled at 37° C., through which a mixed gas (95%O₂—5%CO₂) was bubbled. First, histamine or leukotriene D₄ was added to an organ bath to measure its dose-response. After the ileum piece was washed several times with the buffer, a test compound (will be identified by its example number; this will apply likewise hereinafter) of a predetermined specific concentration was added. Subsequent to incubation for 30 minutes, the dose-response of histamine or leukotriene D₄ was measured again. Incidentally, in Table 7, the values (%) indicate contraction inhibition rate at 10$^{-5}$M, while the values in parentheses show pD'$_2$ values in the case of antihistaminic action and IC$_{50}$ values in the case of anti-LTD₄ action.

TABLE 7

| Test comp'd | Antihistaminic (%) (10$^{-5}$M) | Anti-LTD₄ action (%) (10$^{-5}$M) |
|---|---|---|
| 6 | 37 | 98 (4.6 × 10$^{-7}$) |
| 17 | 100 (pD'$_2$ 5.35) | 96 (1.5 × 10$^{-6}$) |
| 33 | 65 (pD'$_2$ 5.25) | 100 (1.3 × 10$^{-7}$) |
| 35 | 16 | 87 (1.7 × 10$^{-6}$) |
| 39 | 100 (pD'$_2$ 6.42) | 98 (4.4 × 10$^{-7}$) |
| 89 | (pD'$_2$ 5.09) | (2.40 × 10$^{-7}$) |
| 96(b) | 98 (pD'$_2$ 6.17) | (1.20 × 10$^{-7}$) |

Test 2

Antihistaminic Action and Anti-LTD₄ Action (In vivo Tests)

After the hair on the back of a male Hartley guinea pig was cut off, a test compound was orally administered at 10 mg/kg. One hour later, 5% Evans Blue solution was intravenously administered at 1 ml/kg and immediately after that, a 0.3 μg/ml solution of histamine and a 0.5 μg/ml solution of leukotriene D₄ were intracutaneously administered each in an amount of 0.1 ml to the back. Thirty minutes later, the guinea pig was sacrificed under exsanguination, the skin was cut off, and the transudated color was quantitated by extraction. To a control, 0.5% CMC (carboxylmethylcelluose) was orally administered and the subsequent procedures were repeated likewise. From the difference in the amount of the transudated color between the control and the group administered with the test compound, an inhibition rate was calculated.

TABLE 8

| Test comp'd | Anti-H₁ action (%) | Anti-LTD₄ action (%) |
|---|---|---|
| 6 | — | 12 |
| 10 | 36 | 32 |
| 15 | 17 | 37 |
| 17 | 19 | 21 |
| 30 | 40 | 44 |
| 33 | — | 40 |
| 35 | — | 11 |
| 78 | — | 32 |

Test 3

1) H₁ Receptor Binding Inhibition Test

Incubated at 37° C. for 30 minutes was 1 ml of a 50 mM phosphate buffer (pH 7.5) which contained 0.5 nM [$^3$H] mepyramin (activity: 22 Ci/mmol), guinea pig cerebromembranous protein and a test compound. An ice-cooled phosphate buffer was added to terminate the reaction, followed by immediate filtration through a Wattman CF/C filter. The filter was washed twice with 20 ml aliquots of the ice-cooled buffer. The radio-activity of the residue was measured by a liquid scintillation counter. From a measurement value obtained without the addition of the test compound and measurements values obtained upon addition of the test compound at various concentrations, the dose-response of the inhibitory action of the test compound was measured and the 50% inhibitory concentration (IC$_{50}$) was determined. Using the Cheng-Prusoff formula, a dissociation constant was calculated from the IC$_{50}$. In a binding assay, 10$^{-4}$M R(−)dimethindene was used for the measurement of a non-specific binding. From the binding assay, it was found that the receptor was of only one type and that the maximum binding (Bmax) was 278±24 fmol/mg protein. Further, the dissociation constant (K$_D$) of [$^3$H]mepyramin was 3.30±0.26×10$^{-9}$M and when analyzed by a Hill plot, its slope was found to be 1.005.

2) LTD₄ Receptor Binding Inhibition Test

Incubated at 22° C. for 30 minutes was 0.3 ml of a 10 mM piperazine N,N'-bis(2-ethanesulfonate) buffer (pH 7.5) which contained 0.2 nM [$^3$H]leukotriene D₄, guinea pig pulmomembranous protein and a test compound. An ice-cooled tris hydrochloride/sodium chloride buffer (10 mM/100 mM, pH 7.5) was added to terminate the reaction, followed by immediate filtration through a Wattman CF/C filter. The filter was washed twice with 20 ml aliquots of the ice-cooled buffer. The radio-activity of the residue was measured by a liquid scintillation counter. By similar methods as in the H₁ receptor test, the IC$_{50}$ of the test compound was determined and the dissociation constant was calculated. In a binding assay, 2 μM leukotriene D₄ was used for the measurement of a nonspecific binding. From the binding assay, it was found that the receptor was of only one type and that the maximum binding (Bmax) was 988 fmol/mg protein. Further, the dissociation constant (K$_D$) of [$^3$H] leukotriene D₄ was 2.16×10$^{-10}$ M and when analyzed by a Hill plot, its slope was found to be 0.99. Incidentally, the values in Table 9 indicate dissociation constants K$_D$ (mol) or inhibition rates (%) at high concentrations (a: 100 μM, b: 10 μM).

TABLE 9

| Test comp'd | H₁ receptor (%) | LTD₄ receptor (%) |
|---|---|---|
| 1 | — | $1.18 \times 10^{-7}$M |
| 2 | — | $1.56 \times 10^{-6}$M |
| 3 | 44[a] | $5.23 \times 10^{-7}$M |
| 4 | — | 0[a] |
| 5 | 57[a] | $3.16 \times 10^{-7}$M |
| 6 | 18[b] | $8.14 \times 10^{-8}$M |
| 7 | 46[a] | $2.09 \times 10^{-7}$M |
| 8 | $1.45 \times 10^{-4}$M | $3.22 \times 10^{-7}$M |
| 9 | $4.76 \times 10^{-5}$M | $1.48 \times 10^{-7}$M |
| 10 | 50[a] | $1.25 \times 10^{-8}$M |
| 11 | 47[a] | $2.20 \times 10^{-8}$M |
| 12 | 45 | $7.03 \times 10^{-7}$M |
| 13 | — | $3.03 \times 10^{-7}$M |
| 14 | 29[a] | $2.15 \times 10^{-7}$M |
| 15 | 36[a] | 37[b] |
| 16 | 48[a] | $2.50 \times 10^{-6}$M |
| 17 | 40[a] | $2.02 \times 10^{-7}$M |
| 18 | $7.87 \times 10^{-5}$M | $1.10 \times 10^{-6}$M |
| 19 | — | 0[a] |
| 20 | — | 0[a] |
| 21 | 28[a] | 33[b] |
| 22 | 45[a] | $1.24 \times 10^{-6}$M |
| 23 | 41[a] | $5.00 \times 10^{-7}$M |
| 24 | $2.58 \times 10^{-5}$M | $3.01 \times 10^{-7}$M |
| 25 | $5.78 \times 10^{-5}$M | $1.29 \times 10^{-7}$M |
| 26 | — | $5.46 \times 10^{-6}$M |
| 27 | 38[a] | $1.39 \times 10^{-7}$M |
| 28 | 30[a] | $1.40 \times 10^{-6}$M |
| 29 | 34[a] | $3.10 \times 10^{-6}$M |
| 30 | 32[a] | $2.00 \times 10^{-7}$M |
| 31 | $1.98 \times 10^{-5}$M | $3.04 \times 10^{-7}$M |
| 32 | 43[a] | $1.09 \times 10^{-7}$M |
| 33 | 46[a] | $9.70 \times 10^{-9}$M |
| 34 | $1.00 \times 10^{-4}$M | $1.96 \times 10^{-7}$M |
| 35 | $8.79 \times 10^{-5}$M | $2.09 \times 10^{-7}$M |
| 36 | $1.62 \times 10^{-5}$M | $1.35 \times 10^{-7}$M |
| 37 | 28[a] | $2.04 \times 10^{-7}$M |
| 38 | 47[a] | $3.03 \times 10^{-7}$M |
| 39 | $3.74 \times 10^{-5}$M | $4.08 \times 10^{-7}$M |
| 40 | 43[a] | $1.39 \times 10^{-6}$M |
| 41 | $1.28 \times 10^{-4}$M | 34[b] |
| 42 | $8.36 \times 10^{-5}$M | 17[b] |
| 43 | $6.06 \times 10^{-6}$M | $5.51 \times 10^{-6}$M |
| 44 | $8.67 \times 10^{-6}$M | $6.30 \times 10^{-6}$M |
| 45 | 40[a] | 32[b] |
| 46 | $5.95 \times 10^{-6}$M | $6.40 \times 10^{-6}$M |
| 47 | — | $3.35 \times 10^{-7}$M |
| 48 | — | $3.04 \times 10^{-7}$M |
| 49 | — | $4.00 \times 10^{-5}$M |
| 50 | — | $1.08 \times 10^{-6}$M |
| 51 | — | $1.17 \times 10^{-5}$M |
| 52 | — | $3.02 \times 10^{-7}$M |
| 53 | 38[a] | $1.60 \times 10^{-8}$M |
| 54 | 41[a] | $1.29 \times 10^{-7}$M |
| 55 | 43[a] | $3.48 \times 10^{-7}$M |
| 56 | $9.30 \times 10^{-5}$M | 12[a] |
| 57 | $5.79 \times 10^{-5}$M | $8.51 \times 10^{-7}$M |
| 58 | — | 0[a] |
| 59 | 37[a] | 53[a] |
| 60 | 38[a] | $2.23 \times 10^{-7}$M |
| 61 | 28[a] | 27[b] |
| 62 | — | 0 |
| 63 | 40[a] | $3.06 \times 10^{-8}$M |
| 64 | 40[a] | 12[a] |
| 65 | 43[a] | 13[a] |
| 66 | — | 28[b] |
| 67 | 49[a] | 52[a] |
| 68 | 28[a] | $4.28 \times 10^{-7}$M |
| 69 | 33[a] | $3.31 \times 10^{-7}$M |
| 70 | 37[a] | $2.08 \times 10^{-7}$M |
| 71 | 28[a] | 0[a] |
| 72 | — | $4.62 \times 10^{-8}$M |
| 73 | — | 20[b] |
| 74 | — | $2.35 \times 10^{-4}$M |
| 75 | 36[a] | 0 |
| 76 | $1.22 \times 10^{-4}$M | 0[a] |
| 77 | 30[a] | $1.29 \times 10^{-7}$M |
| 78 | 29[a] | $1.26 \times 10^{-5}$M |
| 79 | 43[a] | 42[b] |
| 80 | 36[a] | 27[b] |
| 81 | — | $1.30 \times 10^{-8}$M |
| 82 | 5[b] | $6.00 \times 10^{-8}$M |
| 83 | 0[b] | $3.10 \times 10^{-7}$M |
| 84 | $6.64 \times 10^{-5}$M | $2.60 \times 10^{-8}$M |
| 85 | $5.31 \times 10^{-5}$M | $1.15 \times 10^{-7}$M |
| 86 | 9[b] | $9.28 \times 10^{-8}$M |
| 87 | $6.72 \times 10^{-5}$M | $1.14 \times 10^{-8}$M |
| 88 | $3.11 \times 10^{-5}$M | 30[b] |
| 89 | 6[b] | $4.13 \times 10^{-8}$M |
| 90 | 8[b] | $1.29 \times 10^{-8}$M |
| 91 | $1.20 \times 10^{-7}$M | 37[b] |
| 92 | $1.20 \times 10^{-7}$M | 0[b] |
| 93 | 38[b] | $1.51 \times 10^{-6}$M |
| 94 | 37[b] | $3.15 \times 10^{-7}$M |
| 95 | 33[b] | $6.08 \times 10^{-7}$M |
| 96(a) | 4[b] | 9[b] |
| 96(b) | 14[b] | $3.15 \times 10^{-7}$M |
| 97 | 7[b] | $6.81 \times 10^{-7}$M |

We claim:
1. A phenylene derivative represented by the following formula (1) or a salt thereof:

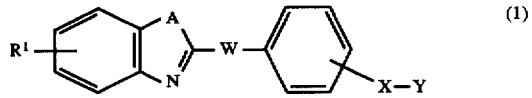

(1)

wherein $R^1$ represents a hydrogen atom or a halogen atom,

A represents —CH=CH—, —CH=N—,

W represents —CH=CH— or —CH$_2$O—,

X represents CH$_2$O—, —CH$_2$S—,

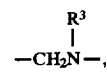

—CH=N—, —COO— or —CONH—, $R^3$ being a hydrogen atom or a lower alkyl group,

Y represents the following formula (a), (b) or (c):

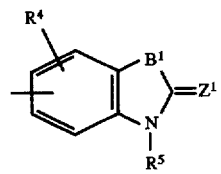

(a)

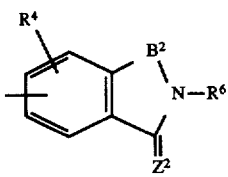

(b)

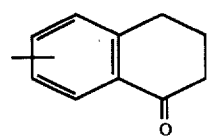

(c)

wherein $R^4$ is a hydrogen atom or a lower alkyl group,
$B^1$ represents

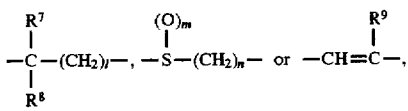

$R^7$ and $R^8$ each being a hydrogen atom or a lower alkyl group, $R^9$ being a hydrogen atom, a cyano group, a halogen atom, a carboxyl group or a tetrazolyl group, l and m being a value of from 0 to 2, and n being a value of 1 to 2, $R^5$ represents a hydrogen atom or a lower alkyl group,
$Z^1$ represents an oxygen atom or a sulfur atom,
$B^2$ represents —$CH_2CH_2$— or —$CH_2CH_2CH_2$—,
$R^6$ represents a hydrogen atom or a lower alkyl group,
$Z^2$ represents an oxygen atom or a sulfur atom, or $Z^2$ and $R^6$ are coupled together with the adjacent nitrogen atom to form a tetrazolyl group.

2. The phenylene derivative or salt thereof according to claim 1, wherein in the formula (1), $R^3$, $R^4$, $R^5$, $R^6$, $R^7$ and $R^8$ are each a hydrogen atom or a $C_{1-6}$ alkyl group.

3. A medicine comprising as an effective ingredient the phenylene derivative or salt thereof according to claim 1 or 2.

4. The medicine according to claim 3, which is a curative for an allergic disease.

5. The medicine according to claim 3, which is a curative for a disease selected from asthma, allergic rhinitis, allergic conjunctivitis, atopic dermatitis, urticaria, psoriasis, rheumatism, inflammatory colitis, cerebral ischemia or cerebral apoplexy.

6. A medicinal composition comprising the phenylene derivative or salt thereof according to claim 1 or 2 and a pharmacologically acceptable carrier.

7. a method for curing a disease selected from asthma, allergic rhinitis, allergic conjunctivitis, atopic dermatitis, urticaria, psoriasis, rheumatism, inflammatory colitis, cerebral ischemia or cerebral apoplexy, which comprises administering an effective amount of the phenylene derivative or salt thereof according to claim 1 or 2 to a patient.

8. A method for treating an allergic disease, which comprises administering an effective amount of the phenylene derivative or salt thereof according to claim 1 or 2 to a patient.

9. A method for treating a disease selected from asthma, allergic rhinitis, allergic conjunctivitis, atopic dermatitis, urticaria, psoriasis, rheumatism, inflammatory colitis, cerebral ischemia or cerebral apoplexy, which comprises administering an effective amount of the phenylene derivative or salt thereof according to claim 1 or 2 to a patient.

10. A method for curing an allergic disease, which comprises administering an effective amount of the phenylene derivative or salt thereof according to claim 1 or 2 to a patient.

* * * * *

UNITED STATES PATENT AND TRADEMARK OFFICE
CERTIFICATE OF CORRECTION

PATENT NO. : 5,756,518
DATED : MAY 26, 1998
INVENTOR(S) : HENK TIMMERMAN, ET AL.

It is certified that error appears in the above-identified patent and that said Letters Patent is hereby corrected as shown below:

Column 34, line 7, "a" should read --A--.

Signed and Sealed this

Second Day of February, 1999

Attest:

*Acting Commissioner of Patents and Trademarks*

Attesting Officer